United States Patent
Kirkin et al.

(10) Patent No.: US 10,023,839 B2
(45) Date of Patent: *Jul. 17, 2018

(54) ANTI-TUMOUR VACCINE DERIVED FROM NORMAL CELLS

(75) Inventors: Alexei Kirkin, Copenhagen (RU); Karine Dzhandzhugazyan, Copenhagen (RU)

(73) Assignee: Cytovac A/S, Horsholm (DK)

(*) Notice: Subject to any disclaimer, the term of this patent is extended or adjusted under 35 U.S.C. 154(b) by 645 days.

This patent is subject to a terminal disclaimer.

(21) Appl. No.: 12/522,048

(22) PCT Filed: Jan. 3, 2008

(86) PCT No.: PCT/EP2008/050050
§ 371 (c)(1),
(2), (4) Date: Dec. 3, 2009

(87) PCT Pub. No.: WO2008/081035
PCT Pub. Date: Jul. 10, 2008

(65) Prior Publication Data
US 2010/0092498 A1    Apr. 15, 2010

(30) Foreign Application Priority Data
Jan. 3, 2007 (GB) .................................. 0700058.1

(51) Int. Cl.
| C12N 5/00 | (2006.01) |
| C12N 5/02 | (2006.01) |
| C12N 5/0783 | (2010.01) |
| A61K 39/00 | (2006.01) |

(52) U.S. Cl.
CPC ........ *C12N 5/0636* (2013.01); *A61K 39/0011* (2013.01); *A61K 2039/5158* (2013.01); *C12N 2501/06* (2013.01); *C12N 2501/23* (2013.01)

(58) Field of Classification Search
None
See application file for complete search history.

(56) References Cited

FOREIGN PATENT DOCUMENTS

WO    WO03/012086    2/2003

OTHER PUBLICATIONS

Shichijo et al., 1996, Jpn. J. Cancer Res. vol. 87: 751-756 Singal et al., 1999, Blood. vol. 93: 4059-4070.*
Quddus et al., 1993, J. Clin. INvest. vol. 92: 38-53 O'Doherty et al., 1994, vol. 82: 487-493.*
Kamath et al., 2000, J. Immunol. vol. 165: 6762-6770.*
Richardson et al., 1990, Clin. Immunol. Immunpath. vol. 55: 368-381.*
Current Protocols in Immunology, Unit 7.10, 1994, pp. 7.10.1-7.10.10.*
Scandella et al., 2002, Blood. vol. 100: 1354-1361.*
Jonuleiet et al., 1997, Eur. J. Immunol. vol. 27: 3135-1342.*
Shahbazian et al., Ann. Rev. Biochem. vol. 76: 75-100.*
Scheinecker et al., 1998, J. Immunol. vol. 161: 3966-3973.*
Kozak et al., 1982,J. Immunol. vol. 128: 1723-1727.*
Richardson, 1986, Hum. Immunol. vol. 17: 456-470.*
Adamopoulou et al., "Human CD4+ T Cells Displaying Viral Epitopes Elicit a Functional Virus Specific Memory CD8+ T Cell Response." Journal of Immunology, vol. 178, No. 9, pp. 5465-5472 (2006).
Kennedy et al., "Direct Cross-Priming by the Lymphocytes Generates Memory Cytotoxic T Cell Responses." Journal of Immunology, vol. 174, No. 7, pp. 3697-3977 (2005).
Xiang et al., "A New Dynamic Model of CD8+ T Effector Cell Responses via CD4+ T Helper-Antigen-Presenting Cells." Journal of Immunology, vol. 174, No. 12, pp. 7497-7505 (2005).
Shichijo et al., "Induction of MAGE genes in lymphoid cells by the demethylating agent 5-aza-2'—deoxycytidine." Japanese journal of cancer research:Gann, vol. 87, No. 7, pp. 751-756 (1996).
Moreira et al., "The histone deacetylase inhibitor Trichostatin A modulates CD4+ T cell responses." BMC Cancer ( Nov. 2003, vol. 3, p. 30.
Luisa et al., "A listing of human tumor antigens recognized by T cells: Mar. 2004 update." Cancer immunology, Immunotherapy, Springer-Verlag, Be, vol. 54, No. 3, pp. 187-207 (2005).
Sarma et al., "cytotoxic T Lymphocytes to an unmutated tumor rejection antigen P1A: normal development but restrained effector function in vivo." The journal of experimental medicine, vol. 189, No. 5, pp. 811-820 (1999).
Groeper et al., "Cancer/testis antigen expression and specific cytotoxic T lymphocyte responses in non small cell lung cancer." International journal of cancer, vol. 120, No. 2, pp. 337-343 (2006).
Sigalotti et al., "Intratumor heterogeneity of cancer/testis antigens expression in human cutaneous melanoma is methylation-regulated and functionally reverted by 5-Aza-2'-deoxycytidine." Cancer research 20041215 US, vol. 64, No. 24, pp. 9167-9171 (2004).
Naota et al., "Generation of peptide-specific CD8<+> T cells by phytohemagglutinin-stimulated antigen-mRNA-transduced CD4+> T cells." Journal of immunological methods, vol. 314, No. 1-2 (2006).

(Continued)

*Primary Examiner* — Amy E Juedes
(74) *Attorney, Agent, or Firm* — Cesari and McKenna, LLP

(57) ABSTRACT

A composition for inducing an immune response in a mammal, comprises lymphoid cells in which expression of tumor antigens has been chemically induced. The tumor antigens are induced in proliferating normal lymphoid cells, especially during the log phase of proliferation. The proliferation of the normal lymphoid cells is stimulated by normal mature dendritic cells. Most conveniently, the lymphoid cells are lymphocytes, especially peripheral blood lymphocytes. The tumor antigens are typically cancer/testis antigens, which may be chemically induced by DNA demethylation. Cancer/testis antigens are expressed in a wide range of tumors, so the composition is able to raise an immune response that is effective against a wide range of tumors, despite the fact that it is derived from normal cells. The composition may be used for preparation of an anti-tumor vaccine for prophylactic or therapeutic use. The composition may also be used for ex vivo activation of cytotoxic T lymphocytes, followed by expansion of the cytotoxic T lymphocyte population by normal dendritic cells, for cancer treatment by adoptive T cell immunotherapy.

4 Claims, 10 Drawing Sheets

(56) References Cited

OTHER PUBLICATIONS

Geiger et al., "A generic RNA-pulsed dendritic cell vaccine strategy for renal cell carcinoma." Journal of translational medicine, vol. 3, No. 1, pp-29 (2005).

Coral et al., "5-aza-2'-deoxycytidine-induced expression of functional cancer testis antigens in human renal cell carcinoma: immunotherapeutic implication." Clinical cancer research: An official journal of the American association for cancer research, vol. 8, No. 8, pp. 2690-2695 (2002).

Guo et al., "De novo induction of a cancer/testis antigen by 5-aza-2'-deoxycytidine augments adoptive immunotherapy in a murine tumor model." Cancer Research, vol. 66, No. 2, pp. 1105-1113 (2006).

Sagaller et al., "Generation od specific anti-melanom reactivity by stimulation of human tumor-infiltrating lymphocytes with MAGE-1 synthetic peptide." Cancer immunology and immunotherapy, vol. 39, No. 2, pp. 105-116 (1994).

Van Rietschoten et al., "Differentially methylated alleles in a distinct region of the human interleukin-1alpha promoter are associated with allele-specific expression of IL-1alpha in CD4+ T cells." Blood, vol. 108, No. 7, pp. 2143-2149 (2006).

Kozlowska et al., "Effect of trichostatin A on CD4 surface density in peripheral blood T cells." Folia histochemica et cytobiologica/ Polish academy of sciences, vol. 44, No. 4, pp. 259-262 (2006).

Mccurdy et al., "Expression of melanoma antigen gene by cells from inflamed joints in juvenile rheumatoid arthritis." The journal of rheumatology, vol. 29, No. 10, pp. 2219-2224 (2002).

Januchowski et al., Effect of hydralazine on CD3-zeta chain expression in Jurkat T cells. Advances in medical sciences, vol. 51, pp. 178-180 (2006).

Richardson et al "Effect of an Inhibitor of DNA Methylation on T Cells. I. 5-Azacytidine Induces T4 Expression on T8+ T Cells." The Journal of Immunology vol. 137, pp. 35-39, 1986.

* cited by examiner

ANTI-TUMOUR VACCINE DERIVED FROM NORMAL CELLS

CROSS-REFERENCE TO RELATED APPLICATIONS

This application is the National Stage of International Application No. PCT/EP2008/050050 filed Jan. 3, 2008, which claims the priority of Great Britain Application No. 0700058.1, filed on Jan. 3, 2007. The contents of both applications are hereby incorporated by reference in their entirety.

FIELD OF THE INVENTION

The invention relates primarily to compositions suitable for inducing immune responses against malignancies; therefore the compositions can be used as a vaccine or for generating cytotoxic cells for adoptive immunotherapy. More particularly, the invention pertains to preparation of a cellular anti-tumor vaccine based on use of only normal cells of the immune system.

BACKGROUND OF THE INVENTION

Advanced cancers represent one of the major causes of human death, but no fully effective methods of treatment have been suggested so far. Cell-based immune therapies represent the most promising non-toxic method of cancer treatment. Cancer immunotherapy aims to destroy tumor cells by immunological mechanisms. It may be used as a sole treatment, or as an adjuvant for other types of therapies such as e.g. surgery, irradiation and chemotherapy. The strategy is based on ex vivo manipulation and reintroduction of cellular products to circumvent immune competences for the purpose of inducing tumor specific immune responses. Thus, the ultimate goal of such cell-based immune therapies is the induction of tumor-specific effector cells and recent advances has focused on CD8+ cytotoxic T lymphocytes (CTL) capable of recognizing and killing tumor cells. It is important that these CTL should be able to survive for a long time in the organism in form of memory cells that can rapidly be reactivated and expanded upon re-appearance of tumor cells in the organism.

The possibility to employ the immune system to attack cancer cells follows from the fact that cancer cells contain new proteins or over-express the existing proteins that may become targets for the immunological attack. Significant number of tumor-associated antigens recognized by such CTLs has been identified since description of the first human tumor antigen MAGE-1 in 1991 by T. Boon's group (Novellino et al., 2005). Three major groups of tumor antigens are currently under intensive investigation as possible targets for active immunotherapy: (i) differentiation antigens such as MART-1, gp100 and tyrosinase for melanomas, and PSA and PSMA for prostate cancer; (ii) overexpressed antigens such as telomerase and survivin and (iii) cancer/testis antigens (CTA) such as MAGE, GAGE, NY-ESO-1 and BORIS.

From the point of specific targeting of immune response to tumor cells, the most perspective are CTA, as they are not expressed in normal cells except germ cells of testis which are not recognized by the immune system (germ cells lack expression of histocompatibility molecules) (see reviews on CTA: (Kirkin et al., 2002; Zendman et al., 2003)). It was demonstrated that activation of CTA in tumor cells is due to promoter demethylation at CpG regions and is a consequence of genome-wide demethylation process that occurs in many cancers, and is correlated with tumor progression (De Smet et al., 1996). Indeed, CTA expression was shown to be associated with tumor progression (Brasseur et al., 1995; Eura et al., 1995; Katano et al., 1997; Patard et al., 1995). Therapeutic potentials of this group of tumor antigens have been confirmed by a number of studies. For example, (a) melanoma patient MZ-2 with metastases was subjected to multiple vaccinations with killed autologous tumor cells leading to development of CTL responses against several CTA (MAGE-1, MAGE-3, GAGE and BAGE, see review (van Pel et al., 1995)) experienced long-lasting disease-free period (P. Coulie, personal communication); (b) vaccination of melanoma patients with dendritic cells loaded with peptide from MAGE-A3 induced regression of antigen-positive metastases (Thurner et al., 1999a); and (c) therapeutic efficiency of polyvalent vaccine correlated with induction of immune response against MAGE-3 antigen (Reynolds et al., 2003). Nevertheless, due to high heterogeneity in the expression of separate CTA members, this group of antigens is not popular as immunological target compared to differentiation or over-expressed antigens.

In order to overcome the problem with heterogenous expression of CTA, vaccines targeting these antigens should be as polyvalent as possible. The patent application WO 03/045427 describes such a polyvalent vaccine targeting CTA that is based on pre-selected human melanoma cell line that express high levels of CTA and do not express melanocyte differentiation antigens. All other tumor cell-based vaccines either employ autologous tumors, or standard cell lines selected on the principle "the more different tumor antigens, the better". Employment of autologous tumor cells in a vaccine as a source of antigens may in some cases induce tumor regression, when it is applied in the form of dendritic cell-based vaccination (O'Rourke et al., 2003; Marshall et al., 2006). The major limitation of the polyvalent vaccine approach is difficulty in production and standardisation of the antigenic mixture. Direct use of original biopsy material lacks standardization, and also as well as such a material is often not available. Use of standard cell lines has not shown high clinical efficiency so far (Palucka et al., 2006; Salcedo et al., 2005).

One of the reasons for low efficiency of using whole tumor cell material is low efficiency of cross-presentation. In order to stimulate generation of the cytotoxic T cells, exogenous tumor protein antigens need to be taken up by antigen presenting cells through the process of endocytosis and then transferred from endocytic vesicles into the cytosol (see review (Cresswell et al., 2005)). This is required for the processing of protein antigens and formation of antigenic peptides. Later on the peptides are presented on the surface in association with MHC class I molecules. Only a small portion of exogenously added antigens enters the cell and only a small fraction of the protein taken up thereafter undergoes cross-presentation. In order to overcome the low efficiency of cross-presentation, several authors suggested use of RNA isolated from tumor cells for transfection of antigen presenting cells (Gilboa and Vieweg, 2004; Schaft et al., 2005; Kyte et al., 2006). The major limiting factor of RNA transfection is lack of formation of complexes of antigenic peptides and MHC class II molecules that is required for induction of T-helper response. Without T-helper response no formation of the CD8+ immunological memory is taking place (Bevan, 2004; Castellino and Germain, 2006), and without formation of memory, CD8+ CTLs die after the initial expansion. In addition, under conditions of tumor growth, formation of CD8+ memory response may be corrupted due to the presence of regulatory cells (Klebanoff et al., 2006).

5-Aza-2'-deoxycytidine (5-Aza-CdR) has been known to induce expression of cancer/testis antigens primarily in tumor cells (Weber et al., 1994). Also, it was previously demonstrated by one group (De Smet et al., 1996) but not another (Weber et al., 1994) that 5-Aza-CdR might also induce expression of at least one of CTA, MAGE-A1, in PHA-activated peripheral blood lymphocytes.

This technique is used in the patent application WO 03/012086 as part of a method of generating antigen presenting cells which comprises collecting cells from a subject, activating the cells with agents such as pokeweed mitogen (PWM) and phytohemagglutinin (PHA), culturing the activated cells ex vivo, and treating the cultured cells with DNA hypomethylating agents so that the cells express multiple tumor associated antigens (CTA). The CTA produced in this way are proposed for use as cancer vaccines. However a major issue in this procedure is the use of foreign agents such as pokeweed mitogen (PWM) and phytohemagglutinin (PHA) for activation the cells.

There is still an unmet requirement for development of effective cell-based vaccine that will be able to overcome these problems and induce productive and long-lasting CTL-mediated anti-tumor immune response.

It is the aim of the present invention to provide a process for preparing antigen presenting compositions by a chemical treatment in which only normal cells are used and no foreign agents are used to activate the cells.

SUMMARY OF THE INVENTION

In its broadest aspect, the present invention provides a composition for inducing an immune response in a mammal, comprising lymphoid cells in which expression of tumor antigens has been chemically induced after activation with mature dendritic cells.

The present invention uses only normal cells i.e. unadulterated lymphoid cells and dendritic cells as isolated from body fluids, thus excluding cells that have been treated with any foreign agents such as plant derived activators e.g. PWM and PHA. Also the present invention does not employ tumor antigen preparations, either synthetic or isolated from tumor cells. As a result the preparation and regulatory approval of a vaccine is much easier and safer. Preferably a patient's own cells are used.

The tumor antigens are induced in proliferating (normal) lymphoid cells, especially during the log phase of proliferation. The proliferation of the normal lymphoid cells is stimulated by (normal) mature dendritic cells.

Most conveniently, the lymphoid cells are lymphocytes, especially peripheral blood lymphocytes.

Preferably the tumor antigens are cancer/testis antigens (CTA), which may be chemically induced by DNA demethylation, for example, by treatment with 5-aza-2'-deoxycytidine. An alternative procedure is that the tumor antigens are chemically induced by histone acetylation, for example, by treatment with histone deacetylase inhibitors such as trichostatin (TSA).

Cancer/testis antigens are expressed in a wide range of tumors, so the composition of the invention is able to raise an immune response that is effective against a wide range of tumors, despite the fact that it is derived from normal cells.

In another aspect the present invention provides use of the composition for stimulating an immune response to the tumor antigens, i.e. for preparation of an anti-tumor vaccine. The vaccine may be used prophylactically or for direct treatment of existing tumors.

The invention provides use of the composition as antigen presenting cells for in vitro activation of cytotoxic T lymphocytes e.g. in adoptive T cell immunotherapy.

In a further aspect the present invention provides a method of preparing tumor-specific CD8+ cytotoxic T lymphocytes which comprises activating T lymphocytes using the composition as antigen presenting cells. The expansion of the cytotoxic cells is preferably induced by (normal) active dendritic cells. The method may be carried out in vivo as a therapeutic procedure or in vitro followed by use of the T cells in adoptive T cell immunotherapy.

DETAILED DESCRIPTION OF THE INVENTION

Figure 1:
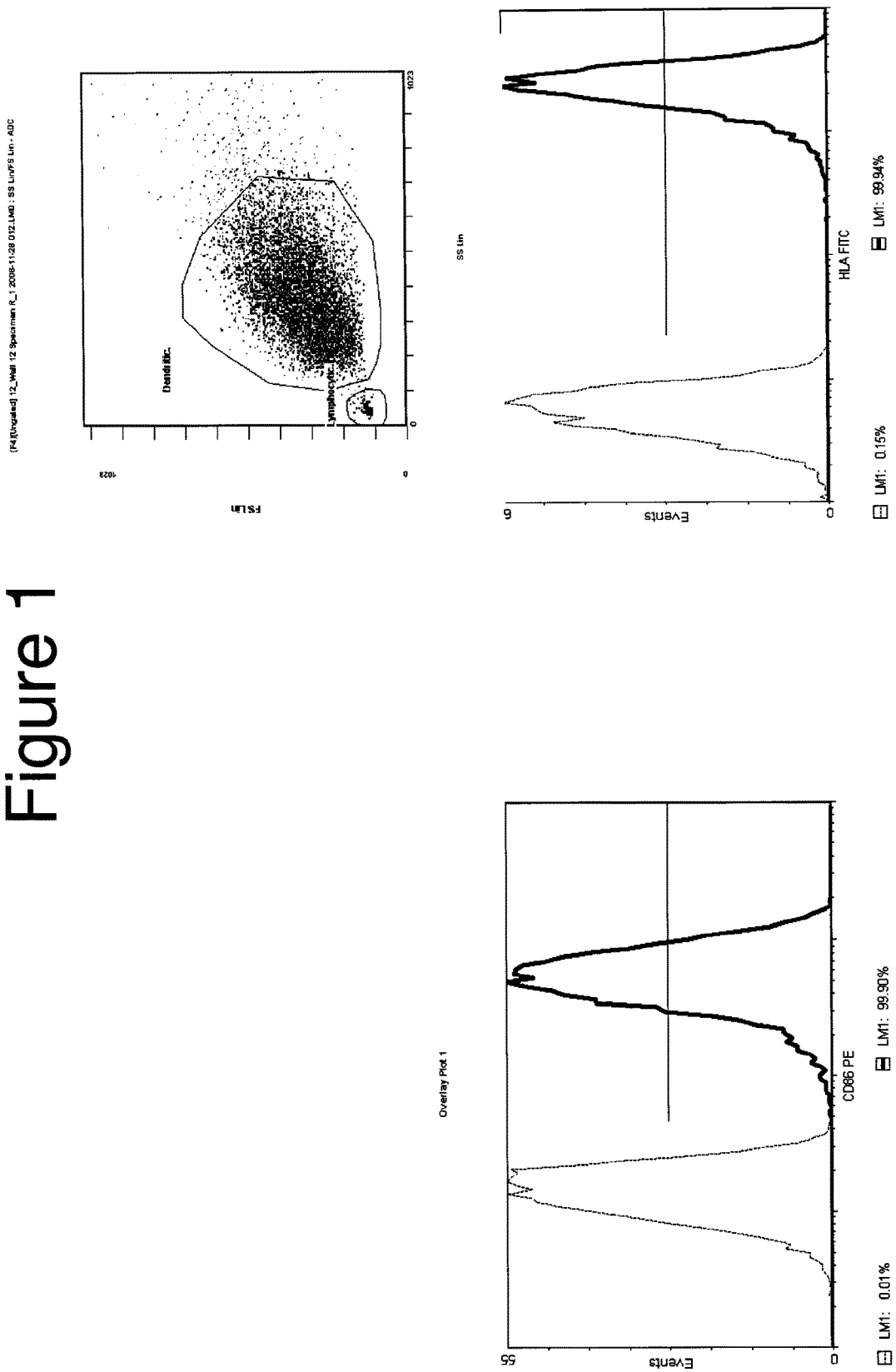
FIG. 1 illustrates phenotype of mature dendritic cells.

The present invention aims to provide an effective immune response by procedures in which the antigen-presenting cells are normal cells in which expression of tumor-associated antigens has been chemically induced, and also which are enriched in CD4+ cells, and so able to directly stimulate cytotoxic T lymphocytes and provide CD4+ mediated help which is vital for formation of the immunological memory. These antigen-presenting cells may be used as a cell based vaccine for in vivo stimulation of an immune response or in adoptive T cell therapy in which cytotoxic T lymphocytes are stimulated in vitro.

The invention is based on the finding that normal lymphoid cells can be induced to proliferate by mature dendritic cells, and during proliferation can be induced by chemical treatment to express tumor antigens, such as canter/testis antigens, resulting in a composition that contains CD4+ cells, and so is capable of presenting tumor antigens to T-cells to generate cytotoxic CD8+ cells, some of which include CD62L memory cell markers.

The normal lymphoid cells are most conveniently lymphocytes, especially peripheral blood lymphocytes, which can be induced by treatment with DNA demethylating agents to express cancer/testis antigens.

Accordingly, by use of preferred aspects of the invention it is possible to propose various routes of cancer treatment, such as:

a method of treating cancer by stimulating an immune response against tumors, comprising:
stimulating proliferation of lymphoid cells by mature dendritic cells,
treating the proliferating lymphoid cells to induce expression of cancer/testis antigens, thereby obtaining an antigen-presenting composition including lymphocytes enriched in CD4+ cells, and
administering the antigen-presenting composition to a cancer patient to stimulate an immune response to the cancer/testis antigens; or alternatively a method of treating cancer by adoptive T cell therapy, comprising:
stimulating proliferation of lymphoid cells by mature dendritic cells,
treating the proliferating lymphoid cells to induce expression of cancer/testis antigens, thereby obtaining an antigen-presenting composition containing normal lymphocytes enriched in CD4+ cells,
using the antigen-presenting composition to activate T cell lymphocytes ex vivo which can be expanded to obtain a cytotoxic composition containing tumor-specific CD8+ cytotoxic T lymphocytes with CD62L memory cell markers, and administering the cytotoxic composition to a cancer patient.

The expansion of the cytotoxic composition is also conveniently achieved by using normal mature dendritic cells to stimulate proliferation.

Most suitably the lymphoid cells are peripheral blood lymphocytes extracted from heterologous or autologous blood.

In its preferred practical implementation, the present invention comprises the following procedures:
A isolation of peripheral blood lymphocytes;
generation of mature dendritic cells from monocytes;
B stimulation of the lymphocytes by the mature dendritic cells leading to preferential proliferation of CD4+ cells;
treatment of the activated lymphocytes with chemical agents leading to induction of expression of cancer/testis antigens;
and
C preparation of vaccine from activated and treated lymphocytes;
use of vaccine as a prophylactic or direct treatment of tumors.
or
D generation of cytotoxic lymphocytes by co-cultivation of lymphocytes with activated and treated lymphocytes;
expansion of cytotoxic lymphocytes in the presence of dendritic cells as feeder cells;
use of cytotoxic lymphocytes for treatment of tumors by adoptive immunotherapy.

While the invention has been described with reference to treatment of cancer in humans, the procedures of the invention are also applicable to veterinary medicine for generating materials for treatment of tumors in non-human mammals.

The invention will be more fully understood by considering the methodology adopted by the present inventors in developing the above findings, as follows.

The principal difference between the cell-based vaccine described in this invention and other existing vaccines designed to induce anti-tumor immunity is that the procedures of this invention do not employ any tumor antigen preparation, either synthetic or isolated from tumor cells. In this new vaccine, tumor antigens are induced endogenously in proliferating antigen-presenting cells of the immune system by chemical treatment. In this way the immune response with formation of tumor antigen-specific CTLs is initiated without need of antigen uptake and cross-presentation. The problem with induction of T helper response is solved by employment of activated T helper cells (CD4+ lymphocytes) functioning both as antigen presenting cells and to provide help to antigen-specific CD8+ cells. By using this approach it is possible to induce expression of a broad spectrum of tumor-associated cancer/testis antigens in proliferating CD4+ cells, and these cells are able to stimulate formation of cytotoxic T lymphocytes recognizing a broad spectrum of tumor cells. The immune CTLs cells induced in this way also have some characteristics of memory cells.

The first task addressed by the present inventors was how to generate a culture of proliferating lymphocytes enriched in CD4+ T cells. It is well known that the best way of generating antigen-specific T-helper cells is to employ mature dendritic cells loaded with the antigen (Jonuleit et al., 2001; De Vries et al., 2003). However, the present inventors mixed antigen-unloaded mature dendritic cells with a non-adherent fraction of lymphocytes and found that after 7-8 days of incubation, there was an intensive proliferation of lymphocytes. The proliferating cultures were mainly T lymphocytes enriched in CD4+ lymphocytes.

Having developed a method of generating cultures of proliferating lymphocytes, the present inventors attempted to induce expression of cancer/testis antigens in these cultures. 5-aza-2'-deoxycytidine (5-Aza-CdR) has been known to induce expression of cancer/testis antigens primarily in tumor cells (Weber et al., 1994). Also, it was previously demonstrated by one group (De Smet et al., 1996) but not another (Weber et al., 1994) that 5-Aza-CdR might also induce expression of at least one of CTA, MAGE-A1, in PHA-activated peripheral blood lymphocytes. It is generally accepted that it is much more difficult to induce expression of CTA in normal cells compared to cancer cells (De Smet et al., 1996; Weber et al., 1994), or that these antigens are not inducible by 5-Aza-CdR in normal cells (Karpf et al., 2004). Nevertheless, after optimizing conditions for lymphocyte growth and their treatment, the present inventors were able to induce all the cancer/testis antigens that they had chosen as the ones most commonly expressed in tumors, namely the CTA's: MAGE-A1, MAGE-A3, MAGE-A4, MAGE-A6, MAGE-A10, MAGE-A12, GAGE-3-7, NY-ESO-1 and BORIS.

Having obtained expression of a broad spectrum of CTA, that resembled their expression in progressed cancer cells, experiments on induction of CTL response were performed. All experiments were done using lymphocytes from HLA-A2+ healthy donors, as in this case it is possible to use HLA-A2-positive tumor cells for detection of anti-tumor CTL response. 5-Aza-CdR-treated lymphocytes were used as stimulators without irradiation or mitomycin C treatment, as their own proliferative capacity was practically absent in the end of 5-Aza-CdR treatment period. The non-adherent fraction of lymphocytes, kept frozen after isolation of monocytes, was mixed with 5-Aza-CdR-treated lymphocytes and incubated for 9 days. IL-2 was added at day 2. At the end of this culture period there was an intensive proliferation of lymphocytes. FACS analysis of proliferating cultures indicated that the proportion of CD8+ lymphocytes exceeded the proportion of CD4+ cells by 2 to 5 fold, and that half of the CD8+ cells were expressing the CD62L marker of central memory cells.

There were also a significant number of natural killer (NK) cells which are not unusual for cell cultures after primary stimulation. Therefore in order to detect lytic activity of only the generated CD8+ CTLs, CD8+ cells were isolated. Measurements of cytotoxic activity were performed using a panel of tumor cell lines both positive and negative for HLA-A2 antigens. Cytotoxic activity of cells in the end of the stimulation cycle was low, but it significantly increased after incubation of cells in the presence of IL-2 for 24 hours. The lysis showed HLA-A2 restriction, indicating CTL-mediated lysis, and not NK-mediated lysis.

Thus, it can be concluded that the present inventors have developed a new antigen presenting cell composition for induction of cytotoxic T lymphocyte response with broad anti-tumor specificity and characteristics of memory response. This composition can be employed either for direct vaccination of cancer patients, or for in vitro generation and expansion of cytotoxic T lymphocytes for adoptive immunotherapy.

For the chemical treatment of the normal lymphoid cells, DNA demethylation with 5-aza-2'-deoxycytidine (5-Aza-CdR) is preferred. Other reagents that may be used for DNA demethylation are 5-azacytidine, 5-fluoro-2'-deoxycytidine, and zebularine, which is also a cytidine analogue. Zebularine may produce a similar effect as 5-Aza-CdR (Chong et al., 2003). There are also some non-nucleoside demethylating agents but their effect is weaker than that of 5-Aza-CdR. in triggering, for example MAGE-1 expression in tumor cells (Chong et al., 2005).

An alternative chemical treatment for inducing antigens is histone acetylation which may be achieved by using histone deacetylase inhibitors. Most commonly used and best studied is Trichostatin A (TSA). It may induce a weak expression of some proteins, including cancer/testis antigens, but the spectrum of these antigens may not completely overlap those expressed by 5-Aza-CdR). If employed together, these reagents may induce a strong expression of "silenced" genes which may exceed an additive effect (Wlachnewski et al., 2006). Another group of histone deacetylase inhibitors are some depsipeptides that also can be used in combination with 5-Aza-CdR (Weiser et al., 2001).

The inventors' experimental work has at this stage necessarily used blood from normal donors. When approved for use with patients, the therapies offered by this invention will normally use blood from cancer patients. However, the fact the invention involves inducing antigens in normal cells points to the possibility of generating vaccine from normal donors for treatment of cancer patients. In this case very careful selection of donor-recipient pairs will be needed in order to decrease alloantigen-specific reaction against donor lymphocytes.

Also, the experimental work has used dendritic cells obtained from the same blood samples as the lymphocytes. The use of dendritic cells other than from the same person would be much more convenient, but creates a problem of safety testing of the donor's dendritic cells. In addition, it is possible that traces of allo-antigens derived from dendritic cells may be acquired by lymphocytes that, in turn, may stimulate allo-response in addition to response to tumor antigens, possibly leading to decrease in tumor-specific response.

In clinical use of the invention, the compositions may include conventional adjuvants as desired or necessary. For example, antigen presenting compositions are sometimes used together with separate injection of IL-2, but more often as a cellular composition alone. Cytotoxic lymphocyte compositions are usually used together with injection of adjuvants such as IL-2. In addition, injection of cytotoxic lymphocyte composition is sometimes preceded by chemotherapy (such as a combination of cyclophosphamide and fludarabine) leading to lymphodepletion. For injection, cells are usually suspended in phosphate-buffered saline supplemented with human serum albumin or autologous plasma. Further information on a delivery formulation can be seen in reviews on the adoptive T cell therapy, for example, (Gattinoni et al, 2006; Yee, 2005).

Interleukins such as IL-2 may also be used to enhance the proliferation of lymphocytes. They are optional, and different interleukins could be used. For example, IL-7 and IL-15 could be used instead of IL-2. Generation of dendritic cells from monocytes usually requires the presence of cytokines, with GM-CSF being the most preferred, although others could be substituted.

The practice of the invention is further illustrated in the following experimental Examples.

Example 1. Generation of Proliferating Cultures of Lymphocytes Enriched in CD4+ Cells In order to induce expression of CTA in antigen presenting cells by chemical treatment (for example, with Aza-5-CdR), this culture should be proliferating. Professional antigen presenting cells, dendritic cells, do not proliferate under normal conditions, and therefore the inventors were looking for another type of antigen presenting cells. There are several types of antigen-presenting cells that may stimulate antigen-specific activation of CD8+ T lymphocytes. In particular, it has been shown that activated CD4+ helper T cells may be employed as antigen-presenting cells (Naota et al., 2006; Kennedy et al., 2005). Additional advantage of CD4+ cells as antigen presenting cells is that they are able to stimulate formation of memory CD8+ cells (Kennedy et al., 2005). The present inventors therefore first decided to optimize the preparation of proliferating cultures of CD4+-enriched lymphocytes. In the example described below the addition of mature dendritic cells to cultures of lymphocytes isolated from peripheral blood was successfully employed.

Preparation of Mature Dendritic Cells was Done According to the Original Methods (Romani et al., 1994; Thurner et al., 1999b) in modifications. The buffy coat components removed from donated blood were obtained from the local Blood Bank. Upon arrival, buffy coats were transferred into the flask with 60 ml of Ca-free and Mg-free Dulbecco's Phosphate Buffered Saline (DPBS, Product No. BE17-512F, Cambrex, Belgium), and approx. 30 ml were layered on 15 ml of Lymphoprep (Product No. 1053980, AXIS-SHIELD PoC AS, Norway) in 50-ml tubes. After centrifugation at 460 g, 30 min, 20° C., the upper layer containing diluted plasma (approx. 40%) was collected for further use as additive to culture medium and for freezing of cells. After addition of heparin (25 IU/ml final), plasma was centrifuged at 1500 g for 15 min and kept frozen at −80° C. until use. Mononuclear cells were collected from the interface of the Lymphoprep gradient in 25 ml of pre-cooled DPBS-EDTA (Cambrex) and washed four-five times with pre-cooled DPBS-EDTA by centrifugation first at 250 g, then at 200 g, and then at 150 g, each time for 12 min at 4° C. After last washing, cells were re-suspended in RPMI 1640 medium (Cambrex) and counted using the Coulter Counter, model Z2. The concentration of lymphocytes and monocytes were determined by gating the corresponding peaks of cells. The cell suspension was frozen in aliquots each containing approx. $10^7$ of monocytes and a variable number of lymphocytes in the freezing medium consisting of 90% of the diluted plasma and 10% of DMSO. Cell suspensions were placed freezing boxes (Nalgen) at −80° C. and were stored at this temperature for up to 6-9 months. All cultures were established from the frozen mononuclear cells. Generation of dendritic cells was performed in T25 tissue culture flasks pre-treated with 5 ml of 5% human serum in RPMI 1640 medium for at least 30 min before experiment. 1 ampoule of the frozen mononuclear cells was thawed in water bath (37° C.), 1 ml of cell suspension was immediately diluted in 13 ml of pre-warmed AIM-V medium (Gibco, Invitrogen). Pre-treatment medium was removed from the flasks and immediately replaced by 7 ml of cell suspension. After 45 min of incubation at 37° C., non-adherent lymphocytes were collected, and adherent monocytes were rinsed twice with pre-warmed RPMI 1640 medium. After addition of 5 ml of AIM-V medium containing 0.5% plasma the flasks were placed in a CO2-incubator at 37° C. The collected lymphocytes were centrifuged and re-suspended in the freezing medium consisting of AIM-V (70%), human serum (20%) and DMSO (10%) and frozen down. After overnight incubation (day 1), GM-CSF and IL-4 (both from Gentaur, Belgium) were added to the cells at a final concentrations of 100 ng/ml and 25 ng/ml. At day 3, 1 ml of AIM-V with 0.5% of plasma was added together with GM-CSF and IL-4 at final concentrations of 100 ng/ml and 25 ng/ml. At day 4, a maturation cocktail consisting of IL-1beta (10 ng/ml), IL-6 (1000 IU/ml), TNF-alpha (10 ng/ml) (all from Gentaur) and PGE2 (Sigma) (1 μg/ml) was added. At day 5 or 6, non-adherent cells were harvested, counted and either used for experiment, or were frozen in aliquots of $10^6$ cells in the freezing medium consisting of AIM-V (70%), human serum (20%) and DMSO (10%).

The purity of generated dendritic cells exceeded 95%. Phenotyping of dendritic cells was done by staining with the direct conjugated antibodies, HLA-DR, DP, DQ-FITC and CD86-PE (BD Biosciences, Denmark, cat. No. 555516 and 555558) and CD3-FITC (Beckman Coulter, Sweden, pn. IM1281). The recommended isotypic controls were used for the phenotyping of the cells. The cell samples were analyzed using a FC500 MPL Flow Cytometer (Beckman Coulter) and the CXP analytical software (Beckman Coulter). The extent of maturation, defined by proportion of cells with high levels of expression of co-stimulatory molecule CD86 and MHC class II exceeded 95%, as shown in FIG. 1.

Figure 2:
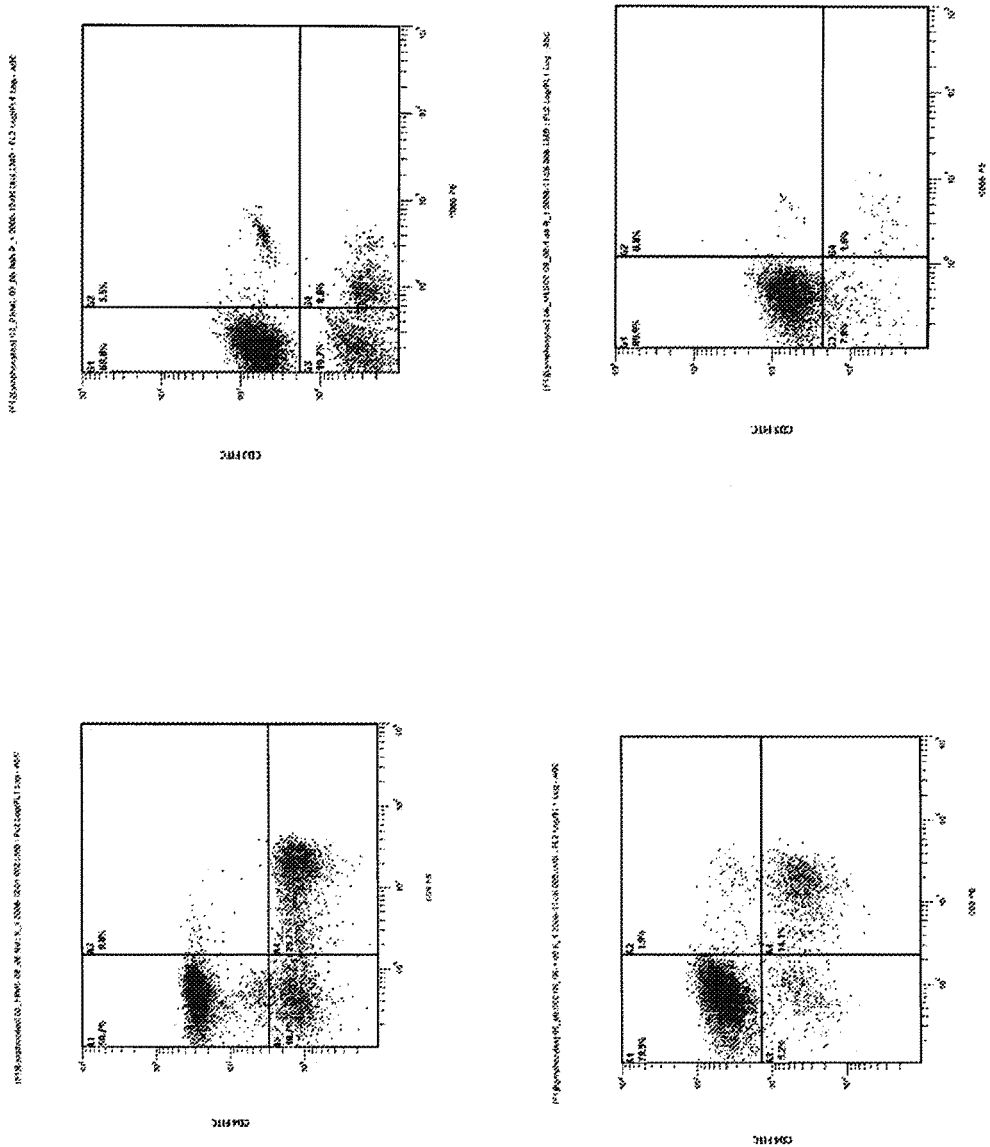
FIG. 2 illustrates phenotype of proliferating culture of lymphocytes obtained after culturing with autologous mature dendritic cells.

For preparation of a proliferating lymphocyte culture, the known property of mature dendritic cells to induce proliferation of autologous lymphocytes was used. The lymphocyte medium consisted of AIM-V medium (Gibco, Invitrogen) and 5% of partially delipidated human AB serum. Delipidation was done according the following procedure. Human serum, stored at −80° C., was thawed overnight in refrigerator and without mixing centrifuged at 3000×g for 1 hr at 4° C. Supernatant was fractionated from bottom into three portions and centrifuged again, as above. Fractions, starting from the bottom, were distributed into new tubes, and remaining floating lipid layer was discarded. The fractions were centrifuged at 29500×g for 1 hr at 4° C. The liquid was collected by a syringe, so that the pellet of inactivated protein and the lipid layer on the top were left in the tube. The combined fractions were sterilized by filtration through 0.2 μm filter and stored frozen at −80° C. in aliquots. Dendritic cells and non-adherent lymphocytes were thawed, washed and re-suspended in lymphocyte medium and 0.1 ml of cell suspension containing $10^4$ dendritic cells and 4-8×$10^4$ lymphocytes was dispensed into wells of U-bottom tissue culture 96-well plate. At days 2 and 5, 0.05 ml of lymphocyte medium containing interleukin 2 (IL-2 final concentration 15 IU/ml) was added into each wells. At day 7 or 8, when lymphocytes reached concentration around $10^6$/ml, cells were harvested and used in the experiments on induction of cancer/testis antigen expression (Example 2). Phenotyping of cell samples was done by staining with the direct conjugated antibodies, CD4-fluorescein isothiocyanate (FITC), CD8-phycoerythrin (PE), CD56-PE, CD3-FITC (BD Biosciences, Denmark, 555346, 555635, 555516 and Beckman Coulter, Sweden, IM1281). Phenotypic characterization of cells performed by flow cytometric analysis indicated increase in proportion of CD4+ cells compared to original culture, as shown in FIG. 2.

Example 2. Induction of Expression of Cancer/Testis Antigens in Proliferating Lymphocytes In preliminary experiments on kinetics and Aza-5-CdR concentration dependence, variable induction of expression of CTA in lymphocyte cultures was observed. Most easily inducible were MAGE-A1, MAGE-A4 and MAGE-A12 (not shown). In order to standardize the conditions of induction, induction of CTA in lymphocytes taken from log phase of cell growth (usually at day 7 or 8, when cell concentration was about $10^6$/ml) was compared with lymphocytes taken from "plateau" (day 9 or 10, when lymphocyte concentration exceeds 2×$10^6$/ml). Lymphocyte population expanded from peripheral blood in the presence of autologous mature dendritic cells was harvested, washed, re-suspended at 0.5×$10^6$/ml in lymphocyte culture medium containing 10 μM of 5-aza-2'-deoxycytidine (Sigma) and 150 IU/ml of IL-2 and placed in the wells of 24-well tissue culture plate in 2 ml per well. Cells were incubated for 3 days, after which they were harvested and counted. Some cells were used in culture with autologous lymphocytes (Example 3), while other were frozen in aliquots as described in the Example 1 for non-adherent lymphocytes. About 2×$10^6$ cells were washed in DPBS and frozen as pellet for RT-PCR analysis.

Expression of individual antigens was detected using RT-PCR analysis identifying expression of RNA coding for these proteins. 2×$10^6$ cells were spun down, the supernatant was discarded, and the pellet was solubilized in 0.3 ml of Cell Lysis Solution (Purescript® RNA isolation kit, Gentra Systems, Minneapolis, Minn.). Total RNA was isolated according to the manufacturer's instructions, precipitated by adding two volumes of 100% isopropanol over the lysis solution, washed with 70% ethanol and re-hydrated in 10 μl RNAase-free distilled water. The isolated RNA was treated by DNAase using the reagents of DNAfree™ kit (Ambion, Austin, Tex.). 1 μl 10× DNAase buffer and 1 μl DNAase (2 units) were added to the sample, the mixture was incubated for 30 min at 37° C., and reaction was terminated by addition of 2 μl DNAase inactivation reagent. cDNA was synthesized using random hexamers, oligo (dT) primers, SuperScript III RNAase H reverse transcriptase kit (Invitrogen Life Technologies, Carlsbad, Calif.) and 10 μl RNA in 20 μl total volume according to the manufacturers' protocol. Reverse transcription (RT) was performed at 50° C. for 60 min, followed by 70° C. for 15 min. Synthesized cDNA was diluted 2-fold by adding equal volume of 10% DMSO in RNAase-free distilled water. Expression profile of MAGE-A1, -A3, -A4, -A6, -A10, and -A12, as well as expression of glyceraldehyde-3-phosphate dehydrogenase (GAPDH) as a positive control for performance of the reaction and for integrity of RNA was detected by PCR using the forward (sense) and reverse (anti-sense) primers described formerly (De Plaen et al, 1994; thor Straten et al, 1997). 1/20 of cDNA was used in PCR amplification in the medium containing 50 mM KCl, 10 mM Tris-HCl, 1.5 mM $MgCl_2$, 0.2 mM cresol, 12% sucrose, 0.5% DMSO, 0.05% BSA, pH 8.6/25° C., 10 pmol of each primer, and during the first cycle at "hot start" added 1.25 U AmpliTaq DNA polymerase (Applied Biosystems, Foster City, Calif.) and 50 µM final concentration of each dNTP, total volume 30 µl. The parameters used for the amplification of MAGE and GAPDH were: initial denaturation 95° C. for 2 min, first cycle 95° C. 30 sec, 80° C. 1-3 min for "hot start", 60° C. 30 sec, and 72° C. 40 sec, followed by 27-36 cycles (94° C. 30 sec, 60° C. 30 sec, and 72° C. 1 min) and 10 min at 72° C. of final extension. For detection of NY-ESO-1, specific fragment 272 by between BLE73 and BLE71 in the gene structure was amplified (Lethe et al., 1998), and $GAGE_{3-7}$, were detected by amplification of specific fragment VV1-VDE24, 244 by (De Backer et al., 1999). Parameters of the reaction for NY-ESO-1 and $GAGE_{3-7}$, after "hot start" were: 32-36 cycles of 95° C. 30 sec, 60° C. 1 min, 72° C. 2 min in the same medium as for MAGE antigens. For amplification of specific fragment 1074 by in human BORIS, the primers selected by (Vatolin et al., 2005), were used. Medium and the first cycle was the same as above excepted 2 U Taq polymerase and 150 µM dNTP in the reaction, and "hot start" followed by 40-45 cycles (94° C. 30 sec, 60° C. 30 sec, 72° C. 2 min) and final extension at 72° C. for 15 min. All reactions were performed in the thermocycler GeneAmp® PCR System 9700 (Applied Biosystems). Negative controls contained aliquots of water instead of cDNA and, in addition, in some experiments on detection of NY-ESO-1 also (minus RT) reaction was performed, where RNA sample after DNAase treatment, but prior to reverse transcription step was used instead of cDNA in order to exclude bands originated not from cDNA. The PCR products were separated together with 100-bp ladder exhibiting 100-bp and 800-bp as most intensive bands (Amersham Pharmacia Biotech) by electrophoresis through 2% agarose gel at 100V, stained with ethidium bromide, visualized under UV illumination and recorded by an image recording system.

Figure 3:
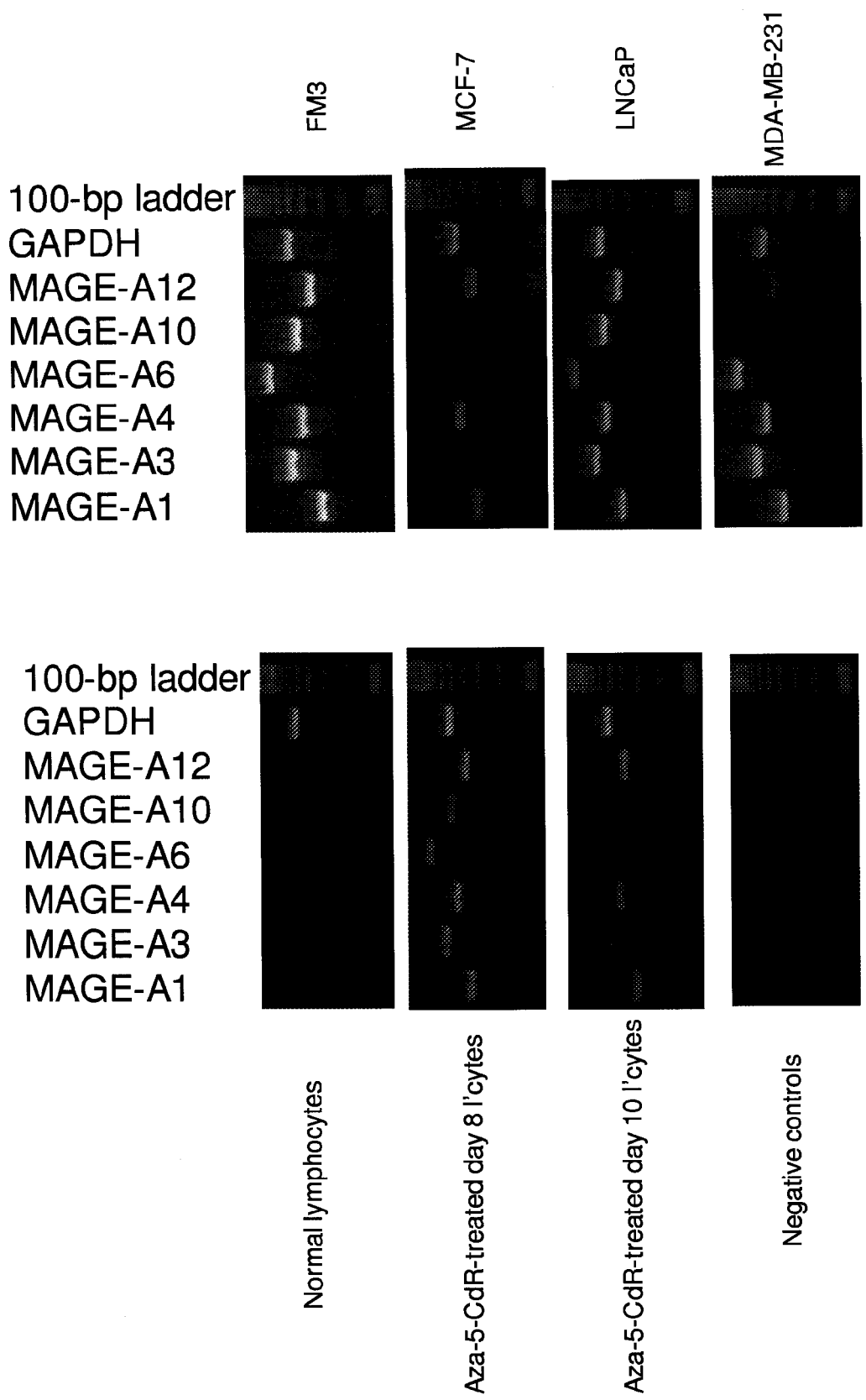
FIG. 3 illustrates expression of antigens of MAGE-A group in intact and 5-Aza-CdR-treated lymphocytes as well as in tumor cells as detected by RT-PCR analysis.
Figure 4:
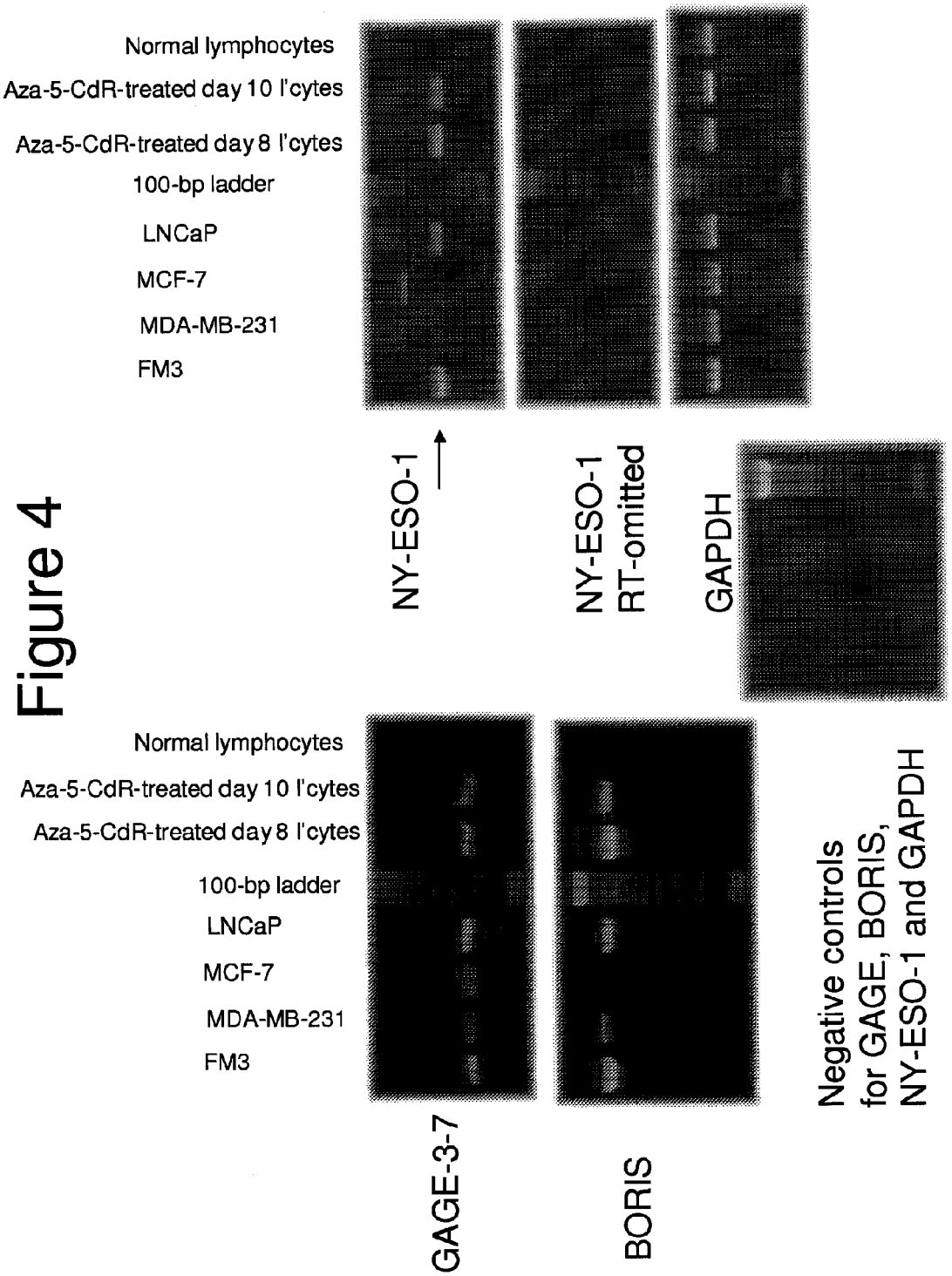
FIG. 4 illustrates expression of NY-ESO-1, GAGE-3-7 and BORIS antigens in intact and 5-Aza-CdR-treated lymphocytes as well as in tumor cells as detected by RT-PCR analysis.

FIGS. 3 and 4 present data on induction of CTA expression in 5-Aza-CdR-treated lymphocytes. For comparison, expression of cancer antigens in tumor cell lines used below in Example 3 is also demonstrated. In this experiment 5-Aza-CdR-treatment of two proliferating lymphocyte cultures is compared: the one taken from log phase of growth (day 8), and the other taken from "plateau" (day 10), where proliferation was stopped due to high cell density. As could be seen, after dilution and treatment by 5-Aza-CdR all the investigated antigens are present in the induced lymphocytes, with higher expression in cultures taken from log phase of growth compared to cells taken from "plateau". This indicates that in order to obtain the highest induction of CTA expression, cells should be taken during the log phase of their growth and high proliferation rate is significant in induction of CTA expression. The resulting CTA expression profile in such lymphocytes cover all tested antigens and is even broader than the profile in some tumor cells.

The expression in the 5-Aza-CdR-treated cells of one group of cancer/testis antigens, MAGE-A antigens also on the protein level, was confirmed by cell-based ELISA. An original procedure described for quantification of gp100 (Erdile et al, 2001) was modified. All cells were washed twice in DPBS containing calcium and magnesium, and after counting were 2-fold titrated and each dilution placed in 4 wells (two for total and two for unspecific binding of ABs). The cells were centrifuged at 1400 rpm for 10 min, and dried, permeablised and fixed with methanol as in the original procedure. For blocking, delipidated HS containing 0.05% sodium azide was used after dilution to 10% by DPBS containing calcium and magnesium. After blocking at 4° C. overnight, wells were incubated for 1 hr at 37° C. and then for 1 hr at r.t. with either anti-MAGE or with isotype-matching control antibodies. As anti-MAGE antibody, hybridoma supernatant of broad-spectrum MAGE-specific 57B clone (kindly provided by Dr. Spagnoli, Switzerland) was used that detects all listed above MAGE antigens excepted MAGE-A10 (Rimoldi et al., 2000). It was diluted 10-fold in 5% HS/azide-DPBS containing calcium and magnesium, and equal IgG concentration of control isotype-matching Abs was added to the control wells. Next, the wells were incubated for 1.5 hr at r.t. with biotinylated goat anti-mouse IgG antibody followed by streptavidine-HRP for 30 min at r.t. (both from "Dako", diluted in 1% BSA-DPBS 500- and 1000-fold, respectively). The wells were washed with 0.05% Tween-DPBS between steps. 100 µl of TMB liquid substrate, supersensitive (Sigma) was used for enzymatic reaction of HRP, and the reaction was terminated by adding an equal volume of 1N HCl. Absorbance of the soluble product was measured at 450 nm with the reference filter 550 nm. Difference between the readings for total and unspecific binding was plotted as specific optical density (OD) in dependence on cell number per well.

For normalization of MAGE proteins expression by total protein amount in each sample of the cell lines, protein was measured the presence of 0.25% Triton X-100 in the aliquots of DPBS-washed cells using bicinchoninic acid (BCA) protein assay kit (Pierce, Rockford, Ill.) and BSA as a standard, according to the procedure recommended by the manufacturer.

Figure 5:
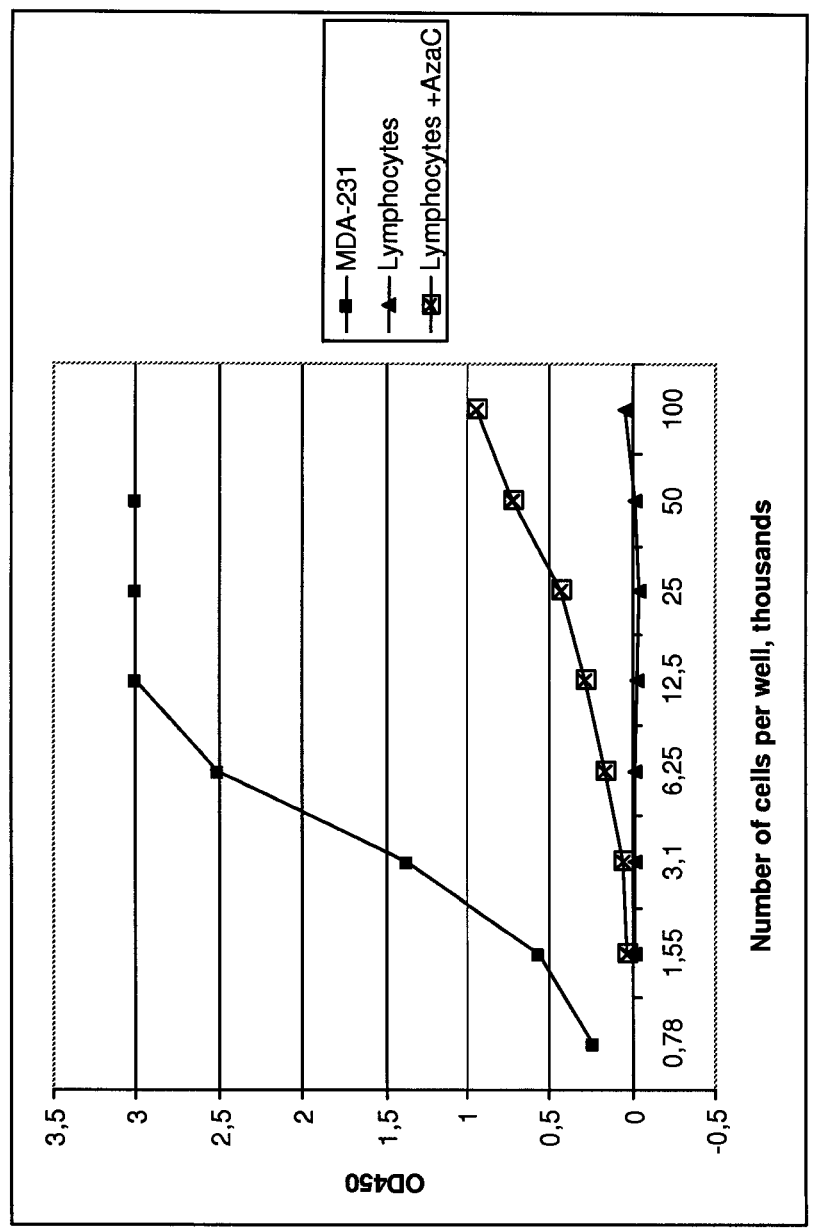
FIG. 5 illustrated protein expression of MAGE-A group in intact and 5-Aza-CdR-treated lymphocytes as well as in tumor cells as detected by cell-based ELISA analysis.

FIG. 5 illustrates the results of cell-based ELISA analysis of MAGE-A expression in untreated and 5-Aza-CdR-treated lymphocytes as well as in breast cancer cell line MDA-MB-231. As can be seen, no expression of MAGE protein is detected in normal lymphocytes, while 5-Aza-CdR-treated lymphocytes express a significant amount of protein, demonstrating induction of expression of MAGE antigens not only on RNA, but also on the protein level. Comparative analysis of the curves for MDA-MB-231 cells and 5-Aza-CdR-treated lymphocytes shows that absolute number of MAGE proteins per cell is about 40-fold higher in tumor cells than in lymphocytes. On the other hand, MDA-MB-231 cells are significantly larger, containing 3.61 mg of total protein per $10^7$ cells as compared to 0.81 mg of protein per $10^7$ lymphocytes (measured by BCA method as described above). Thus, the fraction of MAGEs in the total cellular protein between the progressed, highly MAGE-expressing tumor cell line MDA-MB-231 (FIG. 3) and the 5-Aza-CdR-treated lymphocytes differs less than 10-fold. It is noteworthy that this amount of MAGE proteins is localized intracellularly (in cytosol), and already within antigen-presenting cells, thus, bypassing the low efficient steps of uptake and cross-presentation, which is supposed to be critical for stimulation of tumor antigen-specific CTL response.

Example 3. Induction of Cytotoxic T Cells Response Against 5-Aza-CdR-Treated CD4-Enriched Proliferating Autologous Lymphocytes After induction of CTA in normal lymphocytes after 5-Aza-CdR treatment, these lymphocytes were employed for the generation of tumor-specific immune response in vitro. 5-Aza-CdR-treated cultures were harvested, counted, and seeded in 96-well plate at $20\times10^3$ per well together with $20\text{-}40\times10^3$ of thawed non-adherent autologous lymphocytes in 0.1 ml of lymphocyte medium. After 2 days of incubation, 0.05 ml of lymphocyte medium supplemented with 75 IU/ml of IL-2 was added into each well. Addition of 0.05 ml of lymphocyte medium alone was repeated at days 5 and 7. At day 9, cultures were harvested and counted and used for analysis of immune response. Phenotyping of the cells were done by staining with the direct conjugated antibodies, CD4-fluorescein isothiocyanate (FITC), CD8-phycoerythrin (PE), CD56-PE, CD3-FITC and CD62L-phycoerythrin-cyanide 5 (PC5) (BD Biosciences, Denmark, 555346, 555635, 555516, Beckman Coulter, Sweden, IM1281, IM2655). The recommended isotypic controls were used for the phenotyping of the cells. The cell samples were analyzed using FC500 MPL Flow Cytometer (Beckman Coulter) and the CXP analytical software (Beckman Coulter). The results of analysis of one of such cultures are presented in FIG. 7. As could be seen, the relative proportion of CD8+ cells compared to CD4+ cells has significantly increased as a result of stimulation, showing that these conditions of stimulation promote generation of CD8+ cells. Of special note is a fact that significant part of the generated CD8+ cells expresses CD62L, the marker of central memory cells (Sallusto et al., 2004). On the other side, there were a significant number of double negative cells, among them CD56+NK cells. Therefore, in order to test cytotoxic activity of only generated CD8+ cells, they were isolated using a standard procedure of Miltenyi Biotec, Germany for CD8 T-cell purification. The cells were washed twice by adding cold DPBS buffer (Cambrex, Denmark, BE02-017F) containing 0.5% Foetal Calf serum (Cambrex, DE14-801F) to the cell suspension. After removal of the buffer the cells were magnetically labelled with CD8 Microbeads (Miltenyi Biotec, 130-045-201).

The cell suspension was loaded on a column which was placed in the magnetic field of a MACS Separator. The magnetically labelled CD8 positive cells were retained on the column. The unlabelled cells run through and this cell fraction is depleted of CD8 positive cells. After removal of the column from the magnetic field, the magnetically retained CD8 positive cells were eluted as the positively selected fraction.

Figure 7:
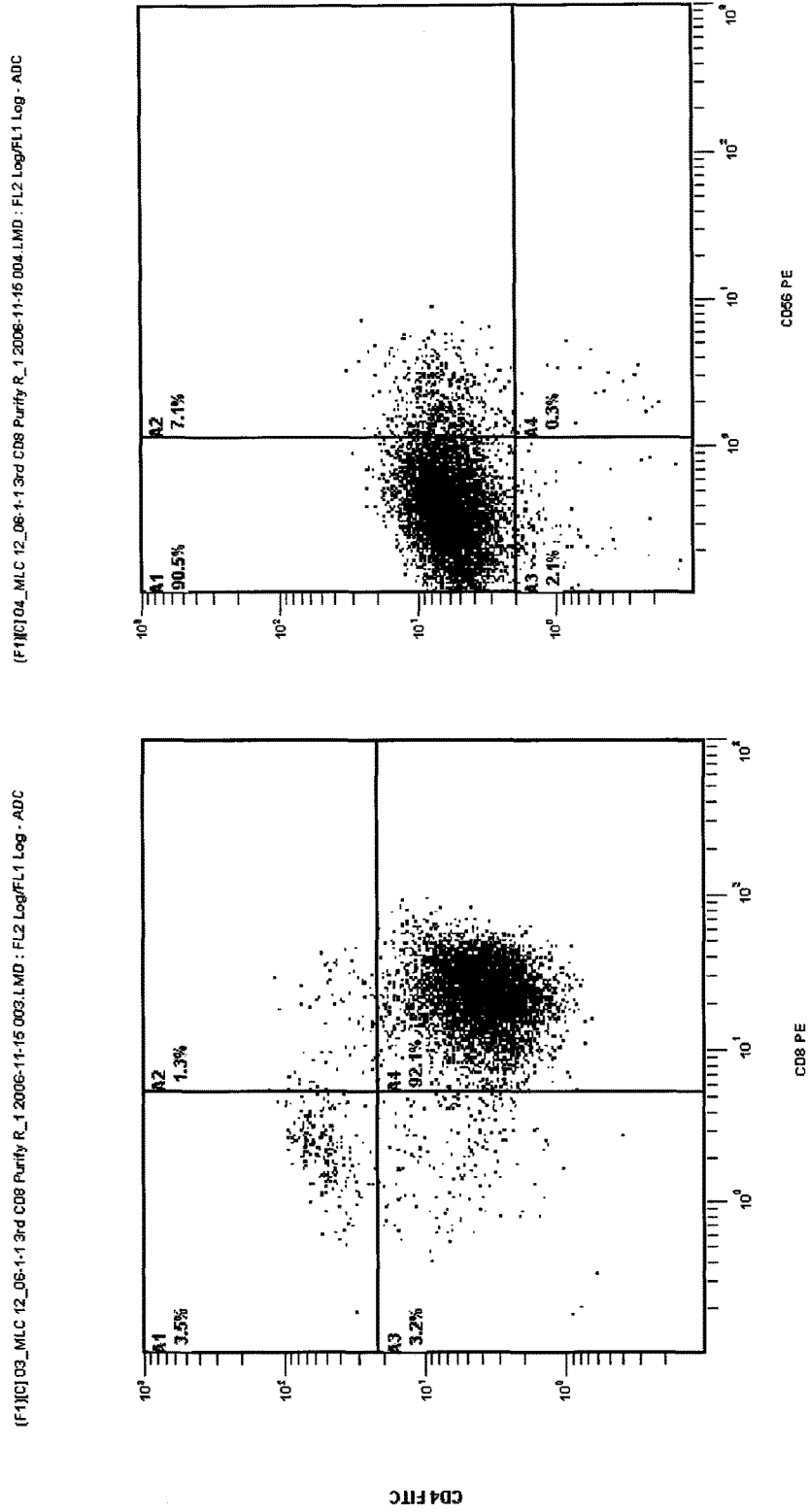
FIG. 7 illustrates phenotype of isolated CD8+ cells.

FIG. 7 illustrate the phenotype of the positively isolated cells, showing that the purity of isolated CD8+ cells is higher than 90%. After isolation, lymphocytes were intensively washed, re-suspended in culture medium supplemented with 25 IU/ml of IL-2 and placed in 24-well plate. After overnight incubation, lymphocytes were harvested, washed once, re-suspended at $1\times10^6$/ml, and added to a panel of prostate and breast cancer cell lines. The following tumor cell lines were used: prostate cancer cell lines: LNCaP (HLA-A2+) and PC3 (HLA-A2-); breast cancer cell lines: MCF-7 (HLA-A2+), MDA-MB-231 (HLA-A2+) and T47D (HLA-A2-). $25\times10^3$ tumor cells were seeded in 48-well plate in 1 ml of RPMI-1640 medium with addition of 10% of FCS and incubated 2 days before test. Before addition of lymphocytes, 0.5 ml of culture supernatant was removed, and 0.25 ml of the suspension of isolated lymphocytes containing $0.25\times10^6$ cells were added to tumor cells. Cells were cultured together for 18-20 hours.

The cytotoxic activity of isolated lymphocytes was determined by detection of production of IFN-gamma in the culture supernatant, as well as microscopic monitoring of disappearance of tumor cells. For INF-gamma determination, 0.35 ml of culture supernatant was collected and kept frozen (−20° C.) until analysis. Concentration of IFN-g in the culture supernatants was measured by sandwich ELISA using "Ready-Set-Go" kit (eBioscience, San Diego, Calif., USA) that included capture Abs, standard, biotinylated detection Abs, and HRP-streptavidin. The procedure was performed essentially according to the manufacturer' recommendations with the following modifications: (1) After overnight binding of capture antibodies to the Nunc Maxisorp 96-well plates and washing of the plates, the blocking step was extended to at least 3 hrs at r.t.; (2) The standard curve was generated by seven serial dilutions of the standard, starting with either 500 or 1000 pg/ml of IFN-g, and the standards and samples in triplicates were incubated at r.t. for 2 hrs followed by incubation at 4° C. overnight. The next steps were performed according to the manufacturers' protocol. Tetramethylbenzidine (TMB) substrate solution from the same kit was used in the enzymatic reaction of HRP, and after terminating the reaction, optical density was measured with wavelength correction as a difference between readings at 450 and 550 nm.

Figure 8:
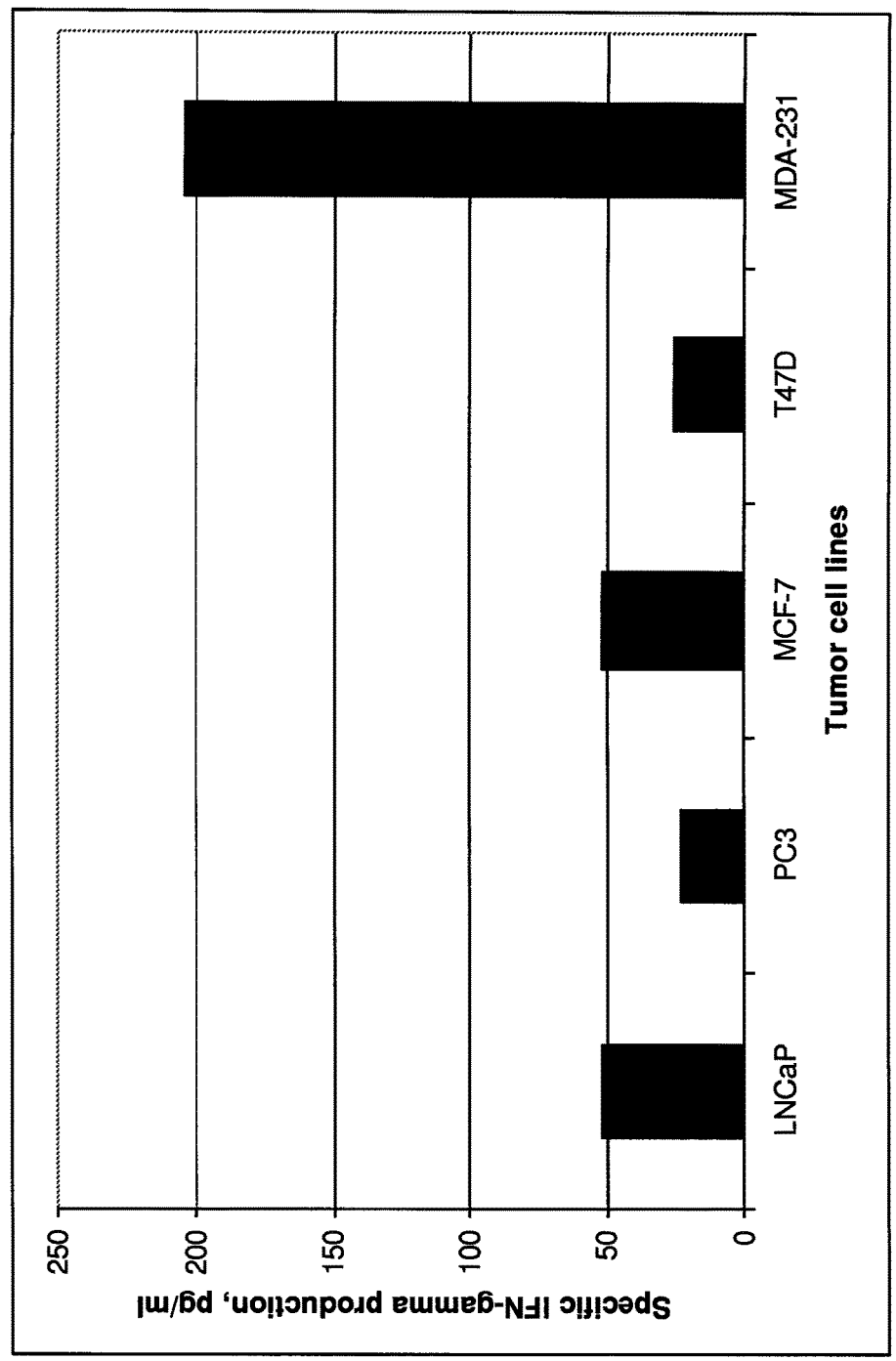
FIG. 8 illustrates production of IFN-gamma after incubation of isolated CD8+ lymphocytes from primary culture with different tumor target cells.

FIG. 8 shows release of IFN-gamma by lymphocytes after overnight incubation with different tumor cells. It is clearly seen that release in the presence of the HLA-A2-positives cell lines LNCaP, MCF-7 and MDA-MB-231 is higher than release in the presence of the HLA-A2-negatives cell lines PC3 and T47D.

Figure 9:
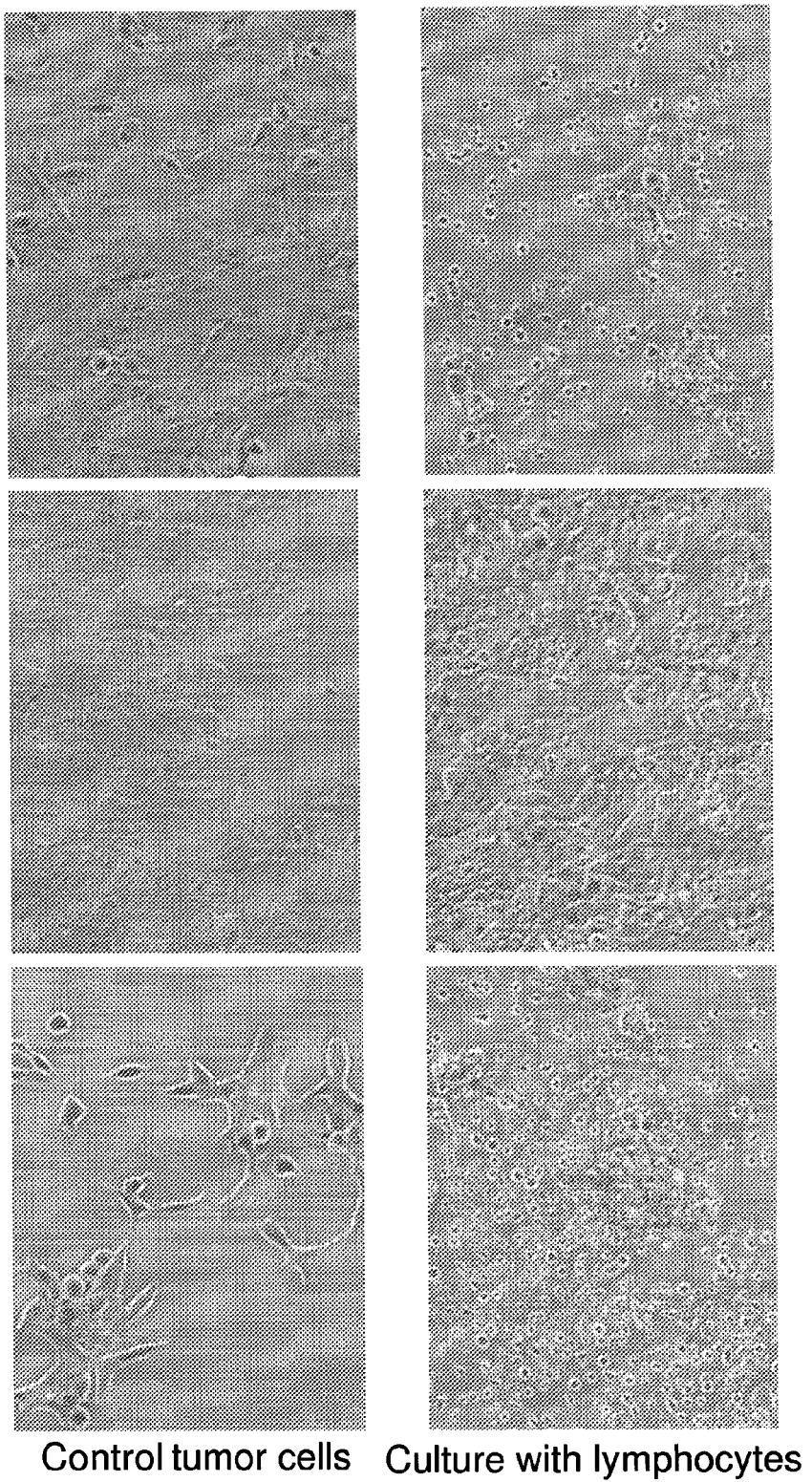
FIG. 9 illustrates microscopically detected killing of different target cells by isolated CD8+ lymphocytes from primary culture.

Microscopic monitoring of the mixed cultures was performed using an inverted microscope equipped with the digital camera. A significant decrease in the number of LNCaP and MDA-MB-231 cells was observed after overnight contact with immune lymphocytes (FIG. 9), while disappearance of MCF-7 cells requires 2-3 days of incubation (not shown).

Figure 6:
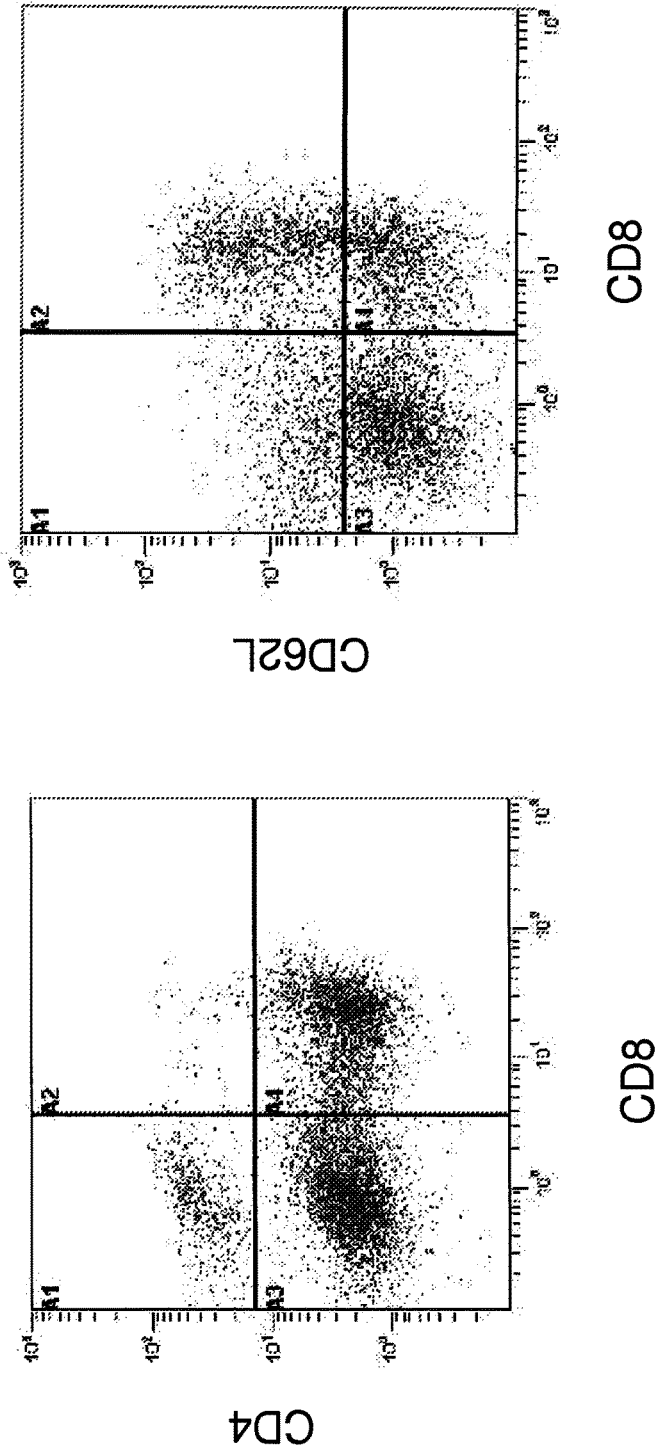
FIG. 6 illustrates phenotype of lymphocytes after primary stimulation with 5-Aza-CdR-treated autologous lymphocytes.
Figure 10:
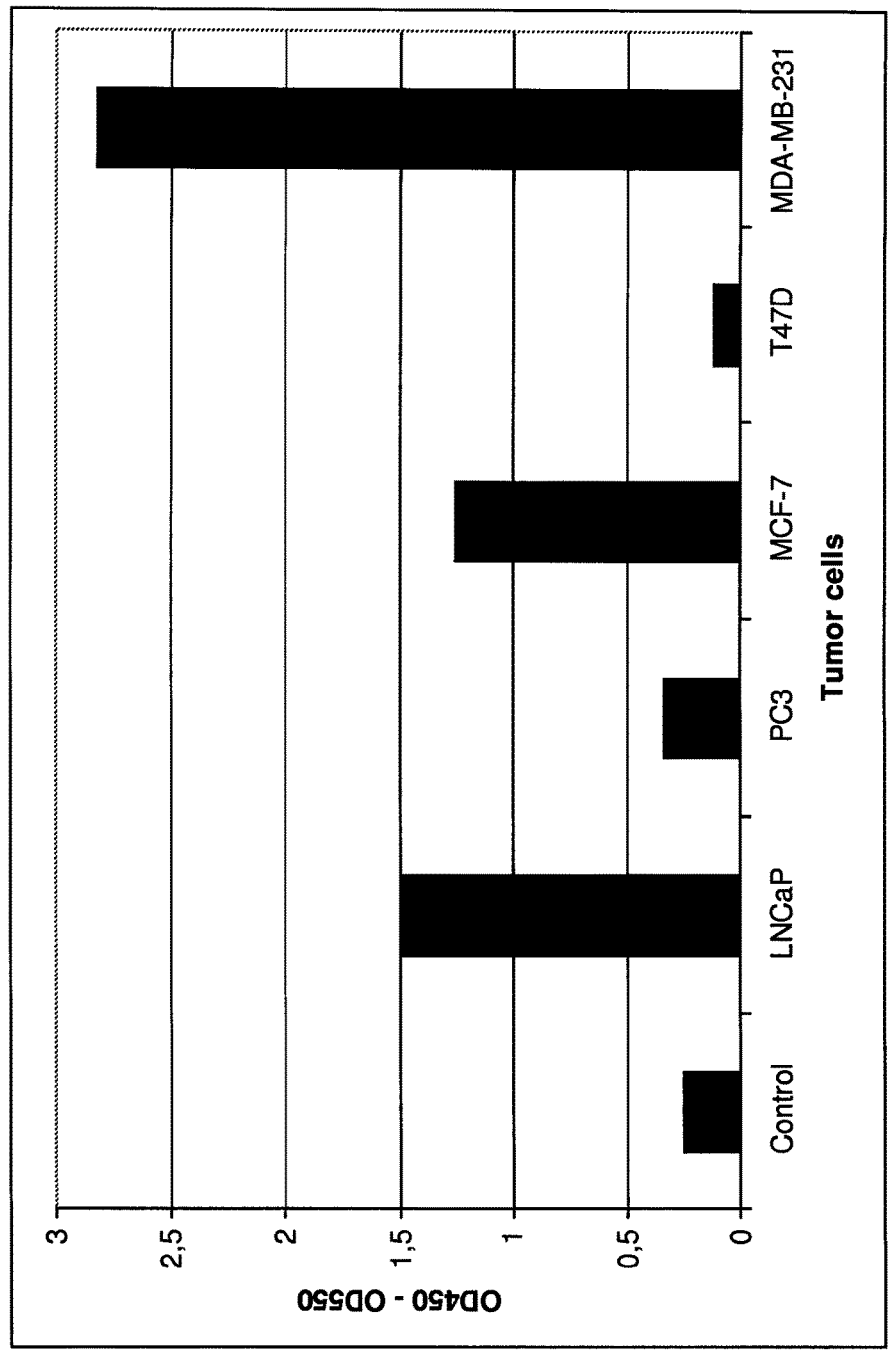
FIG. 10 illustrates production of IFN-gamma after incubation of long-term cultured immune lymphocytes with different target cells.

Some release of IFN-gamma after incubation with HLA-A2-negative cell lines seen at FIG. 8 may be mediated by CD56+NK cells that are still present in the CD8+-enriched lymphocyte population (see FIG. 7). In order to mimic the further development in the patient's organism, in one example lymphocytes were recovered after contact with tumor cells and expanded in the presence of dendritic cells and IL-2. After 3 weeks of expansion, one of such cultures, showing high cytotoxicity against HLA-A2+ tumor cell lines, produced IFN-gamma only in HLA-A2-restricted way (see FIG. 10; note that in this experiment only $0.062\times10^6$ lymphocytes were added to each well with tumor cells). These data indicate that tumor-specific cytotoxic T lymphocytes induced by 5-Aza-CdR-treated CD4-enriched lymphocytes are not damaged as a result of contact with tumor cells. On the opposite, there is a selective proliferation of these lymphocytes leading to enrichment of tumor-specific cytotoxic lymphocytes, reflecting the memory phenotype of CD8+ immune response. This interpretation is in accordance with FIG. 6 in Example 2 demonstrated the presence of the central memory marker CD62L on half of the activated CD8+ cells, and shows that this approach can be used for adoptive immunotherapy.

Example 4. Up-Scaling of the Production of Cytotoxic Lymphocytes for Adoptive Immunotherapy Use of ex vivo generated tumor-specific cytotoxic lymphocytes for adoptive immunotherapy requires establishment of a culture system capable of producing large number of effector cells in a safe way. The procedure described in Example 3 employs 96-well and 24-well plates that make the whole process very laborious and subjected to high risk of contamination. This Example employs two types of large tissue culture flasks: standard T225 tissue culture flasks (Nunc) for generation of dendritic cells and 235 cm² expanded surface flasks (Corning, cat. No 431346) for activation and growing of lymphocytes.

The idea of using of 235 cm² expanded area flasks is based on the observation that growth of lymphocytes is in general better if they are brought into close contact. For example, lymphocytes grow much better in U-bottom 96-well plates than in 24-well flat bottom plates or in T225 tissue culture flasks. In search of tissue culture flasks that might support formation of such tight cell associations, the inventors came across to 235 cm² expanded surface flasks, where the bottom consists of numerous V-form grooves. In the first experiments the inventors compared growth of activated lymphocytes in 96-well plate and 235 cm² expanded surface flask. The results demonstrated that lymphocytes were able to expand in 235 cm² expanded surface flasks with the same efficiency as in 96-well U-bottom plates.

The whole process is adapted to these tissue culture flasks. It employs isolated peripheral blood mononuclear cells and consists of 5 steps: 1) generation of the mature dendritic cells from monocytes, 2) stimulation of lymphocytes by the mature dendritic cells leading to preferential proliferation of CD4+ cells, 3) treatment of the activated lymphocytes with demethylating agent leading to induction of expression of cancer/testis antigens, 4) generation of cytotoxic lymphocytes by co-cultivation of lymphocytes with activated and treated lymphocytes, and 5) expansion of cytotoxic lymphocytes in the presence of autologous dendritic cells as feeder cells.

Generation of the Mature Dendritic Cells.

Isolation of peripheral blood mononuclear cells (PBMC) was carried out as described in Example 1. Isolated cells were not frozen but were used immediately in the experiments. Cell suspension containing 50 millions of monocytes was incubated in T225 tissue culture flask pre-treated for 45 minutes with RPMI 1640 medium supplemented with 5% of human AB serum. After collection of non-adherent lymphocytes the adherent monocytes were washed once and 40 ml of AIM-V medium supplemented with 2% of human AB serum was added into each flask. The collected lymphocytes were frozen in the medium consisting of 70% of AIM-V medium, 20% of human AB serum and 10% of DMSO. GM-CSF (100 ng/ml) and IL-4 (25 ng/ml) were added after overnight incubation and two days later. At day 4, maturation mixture consisting of IL-1beta (10 ng/ml), IL-6 (1000 U/ml), TNF-alpha (10 ng/ml) and prostaglandin E2 (0.1 µg/ml) was added into the flasks. After 2 days, non-adherent cells were harvested and part of them was used for immediate start of activation of lymphocytes while the rest were frozen for further use at the expansion step.

Stimulation of Lymphocytes by the Mature Dendritic Cells.

Non-adherent lymphocytes frozen at the start of culture were thawed, counted, and $40 \times 10^6$ cells were mixed with $4 \times 10^6$ dendritic cells. After centrifugation, this mixture was suspended in 40 ml of lymphocyte cultivation medium consisting of AIM-V medium supplemented with 5% of human AB serum, placed in 235 cm² expanded surface flask and cultured during 8 days. At days 2 and 5, 20 ml of fresh medium supplemented with interleukin 2 (final concentration of 15 U/ml) was added into the flask.

Induction of the Expression of Cancer/Testis Antigens.

At day 8, activated lymphocytes were harvested, counted, and $20 \times 10^6$ cells were centrifuged, suspended in 40 ml of lymphocyte cultivation medium supplemented with 10 µM of 5-aza-2"-deoxycytidine (5-Aza-CdR) and placed in 235 cm² expanded surface flask. After 3 days, cells were harvested, counted, and used as stimulators for generation of cytotoxic lymphocytes.

Generation of Cytotoxic Lymphocytes.

Non-adherent lymphocytes frozen at the start of culture were thawed, counted, and $20 \times 10^6$ cells were mixed with $20 \times 10^6$ of 5-Aza-CdR-treated cells. After centrifugation, this mixture was suspended in 40 ml of lymphocyte cultivation medium consisting of AIM-V medium supplemented with 5% of human AB serum, placed in 235 cm² expanded surface flask and cultured during 11 days. At days 2, 5 and 8, 20 ml of fresh medium supplemented with interleukin 2 (final concentration of 25 U/ml) was added into the flask.

Expansion of Cytotoxic Lymphocytes.

Different protocols are currently used for expansion of activated lymphocytes, and many of them employ feeder cells. In order to block proliferation of feeder cells, they are irradiated. This makes the whole procedure laborious and subjected to the risk of outgrowth of mutated variants. In order to avoid these problems, the inventors decided to use dendritic cells as feeder cells, as mature dendritic cells do not proliferate. In addition it has been shown that autologous dendritic cells are able to support growth of activated lymphocytes (Langhoff and Steinman, 1989). The inventors therefore used dendritic cells generated at day 6 of the reaction and frozen in aliquots for stimulation of growth of cytotoxic lymphocytes. At day 11 of co-incubation of intact lymphocytes with 5-Aza-CdR-treated activated lymphocytes, 60 ml of the culture medium was withdrawn, and $4 \times 10^6$ thawed dendritic cells suspended in 40 ml of the cultivation medium with were added to the culture. At days 13 and 15, culture was split 1:1 with addition of 40 ml of fresh cultivation medium and IL-2. At days 17 or 18, cultures were harvested and characterized by flow cytometry analysis.

The inventors have performed preparation of cytotoxic lymphocytes by this method from lymphocytes isolated from blood of six donors (Table 2). Characterization of cell phenotype of generated lymphocytes by flow cytometry method demonstrates that they have phenotype similar to the one described in Example 3. Three main populations were present: CD8+ lymphocytes, CD4+ lymphocytes and CD3-CD56+ NK cells. Population of CD8+ cells is usually dominant, varying from 17% to 57% (average 40.8%), while proportion of CD4+ cells varies from 2 to 15% except one donor where their proportion was close to 30%. Proportion of NK cells varies from 3% to 54% (average 25.5%). Total number of cells generated after 35 days from the start of reaction varied between $3 \times 10^8$ and $7 \times 10^8$.

TABLE 2

Percentage of main lymphocyte populations in the MLC cultures generated in T235 expanded area flasks.

| Culture | CD4+ CD8− | CD8+ CD4+ | CD56+ CD3− |
|---|---|---|---|
| 51/07-1 | 14.7 | 17.2 | 54.2 |
| 52/07-1 | 12.8 | 57.4 | 15.3 |
| 54/07-1 | 28.8 | 31.2 | 10.5 |
| 59/07-1 | 3.7 | 51.5 | 34 |
| 60/07-1 | 1.9 | 54.9 | 3.3 |
| 61/07-1 | 6.6 | 32.8 | 35.6 |
| Average | 11.42 | 40.83 | 25.48 |

In summary, the described procedure permits generation of large number of cytotoxic lymphocytes employing only tissue culture flasks that permits to perform the whole reaction in a safe and relatively non-laborious way.

This procedure may be easily adapted to the production of tumor-specific cytotoxic lymphocytes in GMP conditions.

REFERENCE LIST

Bevan, M. J. (2004). Helping the CD8+ T-cell response. Nat. Rev. Immunol. 4, 595-602.

Brasseur, F., Rimoldi, D., Liénard, D., Lethé, B., Carrel, S., Arienti, F., Suter, L., Vanwijck, R., Bourlond, A., Humblet, Y., Vacca, A., Conese, M., Lahaye, T., Degiovanni, G., Deraemaecker, R., Beauduin, M., Sastre, X., Salamon, E., Dréno, B., Jäger, E., Knuth, A., Chevreau, C., Suciu, S., Lachapelle, J. M., Pouillart, P., Parmiani, G., Lejeune, F., Cerottini, J. C., Boon, T., and March and, M. (1995). Expression of MAGE genes in primary and metastatic cutaneous melanoma. Int. J. Cancer 63, 375-380.

Castellino, F. and Germain, R. N. (2006). Cooperation between CD4+ and CD8+ T cells: when, where, and how. Annu. Rev. Immunol. 24, 519-540.

Chong J. C., Matsen, C. W, Gonzales, F. A., Ye, W., Greer, S. Marquez, V. E., Jones, P, A, and Selker, E. U. (2003). Inhibition of DNA methylation and reactivation of silenced genes by zebularine. I. Natl. Cancer Inst. 95, 399-409, Chuang. J. C., Yoo, C. B., Kwan. J. M., Li, T. W, Liang, G. Yang, A. S., and Jones, P. A. (2005). Comparison of biological effects of non-nucleoside DNA methylation inhibitors versus 5-Aza-2'-deoxycytidine. Mol. Cancer. Ther. 4, 1515-1520.

Cresswell, P., Ackerman, A. L., Giodini, A., Peaper, D. R., and Wearsch, P. A. (2005). Mechanisms of MHC class I-restricted antigen processing and cross-presentation. Immunol. Rev. 207, 145-157.

De Backer, O., Arden, K. C., Boretti, M., Vantomme, V., De Smet, C., Czekay, S., Viars, C. S., De Plaen, E., Brasseur, F., Chomez, P., Van den Eynde, B. J., Boon, T., and van der Bruggen, P. (1999). Characterization of the GAGE genes that are expressed in various human cancers and in normal testis. Cancer Res. 59, 3157-3165.

De Plaen, E., Arden, IC., Traversari, C Gaforlo, J. J., Szikora, J. P., De Smet, C., Brasseur, F., van der Bruggen, P., Lethe, B, and Lurquln. C. Structure, chromosomal localization, and expression of 12 genes of the MAGE family. Immunogenetics, 4, 360-369.

De Smet, C., De Backer, O., Faraoni, I., Lurquin, C., Brasseur, F., and Boon, T. (1996). The activation of human gene MAGE-1 in tumor cells is correlated with genome-wide demethylation. Proc. Natl. Acad. Sci. U.S.A. 93, 7149-7153.

De Vries, I. J., Lesterhuis, W. J., Scharenborg, N. M., Engelen, L. P., Ruiter, D. J., Gerritsen, M. J., Croockewit, S., Britten, C. M., Torensma, R., Adema, G. J., Figdor, C. G., and Punt, C. J. (2003). Maturation of dendritic cells is a prerequisite for inducing immune responses in advanced melanoma patients. Clin. Cancer Res. 9, 5091-5100.

Dupont, J, Latouche, J B, Ma, C. and Sadelain, M. (2005). Artificial antigen-presenting cells transduced with telomerase efficiently expand epitope-specific human leukocyte antigen restricted cytoxic T cells. Cancer Res 65, 5417-5427.

Erdile, L. F., Smith, D., and Berd. D. (2001). Whole cell ELISA for detection of tumor antigen expression In tumor samples. J Immunol Methods, 258, 47-53.

Eura, M., Ogi, K., Chikamatsu, K., Lee, K. D., Nakano, K., Masuyama, K., Itoh, K., and Ishikawa, T. (1995). Expression of the MAGE gene family in human head-and-neck squamous-cell carcinomas. Int. J. Cancer 64, 304-308.

Gilboa, E. and Vieweg, J. (2004). Cancer immunotherapy with mRNA-transfected dendritic cells. Immunol. Rev. 199, 251-263.

Jonuleit, H., Giesecke-Tuettenberg, A., Tüting, T., Thurner-Schuler, B., Stuge, T. B., Paragnik, L., Kandemir, A., Lee, P. P., Schuler, G., Knop, J., and Enk, A. H. (2001). A comparison of two types of dendritic cell as adjuvants for the induction of melanoma-specific T-cell responses in humans following intranodal injection. Int J Cancer 93, 243-251.

Karpf, A. R., Lasek, A. W., Ririe, T. O., Hanks, A. N., Grossman, D., and Jones, D. A. (2004). Limited gene activation in tumor and normal epithelial cells treated with the DNA methyltransferase inhibitor 5-Aza-2'-deoxycytidine. Mol. Pharmacol. 65, 18-27.

Katano, M., Nakamura, M., Morisaki, T., and Fujimoto, K. (1997). Melanoma antigen-encoding gene-1 expression in invasive gastric carcinoma: correlation with stage of disease. J. Surg. Oncol. 64, 195-201.

Kennedy, R., Undale, A. H., Kieper, W. C., Block, M. S., Pease, L. R., and Celis, E. (2005). Direct cross-priming by Th lymphocytes generates memory cytotoxic T cell responses. J. Immunol. 174, 3967-3977.

Kirkin, A. F., Dzhandzhugazyan, K. N., and Zeuthen, J. (2002). Cancer/testis antigens: structural and immunobiological properties. Cancer Invest 20, 222-236.

Klebanoff, C. A., Gattinoni, L., and Restifo, N. P. (2006). CD8 T-cell memory in tumor immunology and immunotherapy. Immunol. Rev. 211, 214-224.

Kyte, J. A., Mu, L., Aamdal, S., Kvalheim, G., Dueland, S., Hauser, M., Gullestad, H. P., Ryder, T., Lislerud, K., Hammerstad, H., and Gaudernack, G. (2006). Phase I/II trial of melanoma therapy with dendritic cells transfected with autologous tumor-mRNA. Cancer Gene Ther. 13, 905-918.

Langhoff and Steinman, 1989, Clonal expansion of human T lymphocytes initiated by dendritic cells. J. Exp. Med. 169, 315-320.

Lethé, B., Lucas, S., Michaux, L., De Smet, C., Godelaine, D., Serrano, A., De Plaen, E., and Boon, T. (1998). LAGE-1, a new gene with tumor specificity. Int. J. Cancer 76, 903-908.

Liang, G., Gonzales. F. A., Jones, P, A., Orntoft. T P., and Thykjaer, T. (2002). Analysis of gene induction in human fibroblasts and bladder cancer cells exposed to the methylation Inhibitor 5-Aza-2'-deoxycytidine. Cancer Res. 62, 961-966.

Marshall, J. A., Forster, T. H., Purdie, D. M., Lanagan, C. M., O'Connor, L. E., O'Rourke, M. G., Johnson, M. K., See, J. L., Ellem, K. A., Martinez, N. R., Lopez, J. A., and Schmidt, C. W. (2006). Immunological characteristics correlating with clinical response to immunotherapy in patients with advanced metastatic melanoma. Immunol. Cell Biol. 84, 295-302.

Naota, H., Miyahara, Y., Okumura, S., Kuzushima, K., Akatsuka, Y., Hiasa, A., Kitano, S., Takahashi, T., Yuta, A., Majima, Y., and Shiku, H. (2006). Generation of peptide-specific CD8(+) T cells by phytohemagglutinin-stimulated antigen-mRNA-transduced CD4(+) T cells. J. Immunol. Methods. 314, 54-66.

Novellino, L., Castelli, C., and Parmiani, G. (2005). A listing of human tumor antigens recognized by T cells: March 2004 update. Cancer Immunol. Immunother. 54, 187-207.

O'Rourke, M. G., Johnson, M., Lanagan, C., See, J., Yang, J., Bell, J. R., Slater, G. J., Kerr, B. M., Crowe, B., Purdie, D. M., Elliott, S. L., Ellem, K. A., and Schmidt, C. W. (2003). Durable complete clinical responses in a phase I/II trial using an autologous melanoma cell/dendritic cell vaccine. Cancer Immunol. Immunother. 52, 387-395.

Palucka, A. K., Ueno, H., Connolly, J., Kerneis-Norvell, F., Blanck, J. P., Johnston, D. A., Fay, J., and Banchereau, J. (2006). Dendritic cells loaded with killed allogeneic melanoma cells can induce objective clinical responses and MART-1 specific CD8+ T-cell immunity. J. Immunother. 29, 545-557.

Patard, J. J., Brasseur, F., Gil-Diez, S., Radvanyi, F., Marchand, M., Francois, P., Abi-Aad, A., Van Cangh, P., Abbou, C. C., Chopin, D., and Boon, T. (1995). Expression of MAGE genes in transitional-cell carcinomas of the urinary bladder. Int. J. Cancer 64, 60-64.

Reynolds, S. R., Zeleniuch-Jacquotte, A., Shapiro, R. L., Roses, D. F., Harris, M. N., Johnston, D., and Bystryn, J. C. (2003). Vaccine-induced CD8+ T-cell responses to MAGE-3 correlate with clinical outcome in patients with melanoma. Clin. Cancer Res. 9, 657-662.

Rimoldi, D., Salvi, S., Schultz-Thater, E., Spagnoli, G. C., and Cerottini, J. C. (2000). Anti-MAGE-3 antibody 57b and anti-MAGE-1 antibody 6C1 can be used to study different proteins of the MAGE-A family. Int. J. Cancer 86, 749-751.

Romani, N., Gruner, S., Brang, D., Kämpgen, E., Lenz, A., Trockenbacher, B., Konwalinka, G., Fritsch, P. O., Steinman, R. M., and Schuler, G. (1994). Proliferating dendritic cell progenitors in human blood. J. Exp. Med. 180, 83-93.

Salcedo, M., Bercovici, N., Taylor, R., Vereecken, P., Massicard, S., Duriau, D., Vernel-Pauillac, F., Boyer, A., Baron-Bodo, V., Mallard, E., Bartholeyns, J., Goxe, B., Latour, N., Leroy, S., Prigent, D., Martiat, P., Sales, F., Laporte, M., Bruyns, C., Romet-Lemonne, J. L., Abastado, J. P., Lehmann, F., and Velu, T. (2005). Vaccination of melanoma patients using dendritic cells loaded with an allogeneic tumor cell lysate. Cancer Immunol. Immunother. 55, 819-829.

Sallusto, F., Geginat, J., and Lanzavecchia, A. (2004). Central memory and effector memory T cell subsets: function, generation, and maintenance. Annu. Rev. Immunol. 22, 745-763.

Schaft, N., Dorrie, J., Thumann, P., Beck, V. E., Muller, I., Schultz, E. S., Kampgen, E., Dieckmann, D., and Schuler, G. (2005). Generation of an optimized polyvalent monocyte-derived dendritic cell vaccine by transfecting defined RNAs after rather than before maturation. J. Immunol. 174, 3087-3097.

Thurner, B., Haendle, I., Röder, C., Dieckmann, D., Keikavoussi, P., Jonuleit, H., Bender, A., Maczek, C., Schreiner, D., von den Driesch, P., Bröcker, E. B., Steinman, R. M., Enk, A., Kämpgen, E., and Schuler, G. (1999). Vaccination with Mage-3A1 peptide-pulsed mature, monocyte-derived dendritic cells expands specific cytotoxic T cells and induces regression of some metastases in advanced stage 1V melanoma. J. Exp. Med. 190, 1669-1678.

thor Straten, P., Kirkin, A. F., Seremet, T., and Zeuthen, J. Expression of transporter associated with antigen processing 1 and 2 (TAPI/2) in malignant melanoma cell lines. Int. J. Cancer, 70: 582-556, 1997.

Thurner, B., Röder, C., Dieckmann, D., Heuer, M., Kruse, M., Glaser, A., Keikavoussi, P., Kämpgen, E., Bender, A., and Schuler, G. (1999b). Generation of large numbers of fully mature and stable dendritic cells from leukapheresis products for clinical application. J. Immunol. Methods 223, 1-15.

van Pel, A., van der Bruggen, P., Coulie, P. G., Brichard, V. G., Lethé, B., Van den Eynde, B. J., Uyttenhove, C., Renauld, J. C., and Boon, T. (1995). Genes coding for tumor antigens recognized by cytolytic T lymphocytes. Immunol. Rev. 145, 229-250.

Vatolin, S., Abdullaev, Z., Pack, S. D., Flanagan, P. T., Custer, M., Loukinov, D. I., Pugacheva, E., Hong, J. A., Morse, H., III, Schrump, D. S., Risinger, J. I., Barrett, J. C., and Lobanenkov, V. V. (2005). Conditional expression of the CTCF-paralogous transcriptional factor BORIS in normal cells results in demethylation and derepression of MAGE-A1 and reactivation of other cancer-testis genes. Cancer Res. 65, 7751-7762.

Weber, J., Salgaller, M., Samid, D., Johnson, B., Herlyn, M., Lassam, N., Treisman, J., and Rosenberg, S. A. (1994). Expression of the MAGE-1 tumor antigen is up-regulated by the demethylating agent 5-Aza-2'-deoxycytidine. Cancer Res. 54, 1766-1771.

Weiser, T. S., Ohnmachi, G. A., Guo, Z. S, Fischette. M R. Chen, G. A., Hong, J. A. Nguyen, D. M., and Schrump, D. S. (2001). Induction of MAGE-3 expression in lung and esophageal cancer cells. Ann. Thorac. Surg. 71, 295-301.

Wischnewski, F., Pantel, K, and Schwarzenbach, H (2006). Promoter demethylation and histone acetylation mediate gene expression of MAGE-A1, -A2, -A3, and -A12 in human cancer cells. Mol, Cancer Res. 4, 339-49.

Yee, C. (2005). Adoptive T cell therapy: Addressing challenges in cancer Immunotherapy. J. Transl. Med. 3, 17.

Zendman, A. J., Ruiter, D. J., and van Muijen, G. N. P. (2003). Cancer/testis-associated genes: Identification, expression profile, and putative function. J. Cell Physiol 194, 272-288.

The invention claimed is:

1. A method of preparing an antigen-presenting composition enriched in CD4+ cells as compared to CD8+ cells, comprising the steps of obtaining autologous mature dendritic cells from blood monocytes by culturing the blood monocytes with GM-CSF and IL-4 and incubating the cultured blood monocytes with a maturation mixture that includes IL-1beta, TNF-alpha, IL-6, and PGE2, stimulating proliferation of autologous normal non-activated lymphoid cells by coculturing the autologous normal non-activated lymphoid cells with the autologous mature dendritic cells to obtain proliferating cells enriched in CD4+ cells, wherein the ratio between CD4+ and CD8+ cells in the proliferating cells is increased as compared to the ratio between CD4+ and CD8+ cells in the autologous normal non-activated lymphoid cells, and chemically treating the CD4+ enriched proliferating cells with an agent that induces DNA demethylation to induce expression of cancer/testis antigens, thereby obtaining the antigen-presenting composition in which the ratio between CD4+ and CD8+ cells is increased as compared to the ratio between CD4+ and CD8+ cells in the autologous normal non-activated lymphoid cells, wherein the agent that induces DNA demethylation is 5-aza-2'-deoxycytidine, 5-azacytidine, 5-fluoro-2'-deoxycytidine, or zebularine, and the autologous mature dendritic cells are not loaded with the cancer/testis antigens.

2. The method of claim 1, in which the autologous normal non-activated lymphoid cells are peripheral blood lymphocytes extracted from autologous blood.

3. The method of claim 1, in which expression of the cancer/testis antigens are induced during the log phase of proliferation of the proliferating cells.

4. The method of claim 1, wherein the agent that induces DNA demethylation is 5-aza-2'-deoxycytidine.

\* \* \* \* \*